(12) United States Patent
Pan et al.

(10) Patent No.: US 9,150,522 B2
(45) Date of Patent: Oct. 6, 2015

(54) KINASE INHIBITOR AND METHOD FOR TREATMENT OF RELATED DISEASES

(71) Applicants: PEKING UNIVERSITY SHENZHEN GRADUATE SCHOOL, Shenzhen (CN); Beijing Reciprocapharmaceuticals Co. Ltd., Beijing (CN)

(72) Inventors: Zhengying Pan, Shenzhen (CN); Xitao Li, Shenzhen (CN)

(73) Assignees: Peking University Shenzhen Graduate School (CN); Beijing Reciprocapharmaceuticals Co. Ltd. (CN)

(*) Notice: Subject to any disclaimer, the term of this patent is extended or adjusted under 35 U.S.C. 154(b) by 0 days.

(21) Appl. No.: 14/354,302

(22) PCT Filed: Oct. 25, 2012

(86) PCT No.: PCT/CN2012/001432
§ 371 (c)(1),
(2) Date: Apr. 25, 2014

(87) PCT Pub. No.: WO2013/060098
PCT Pub. Date: May 2, 2013

(65) Prior Publication Data
US 2014/0256759 A1   Sep. 11, 2014

(30) Foreign Application Priority Data
Oct. 25, 2011 (CN) .......................... 2011 1 0327240

(51) Int. Cl.
C07D 239/48 (2006.01)
A61K 31/505 (2006.01)
C07D 407/12 (2006.01)
C07D 413/12 (2006.01)
C07D 405/12 (2006.01)

(52) U.S. Cl.
CPC ............ *C07D 239/48* (2013.01); *C07D 405/12* (2013.01); *C07D 407/12* (2013.01); *C07D 413/12* (2013.01)

(58) Field of Classification Search
CPC ........................... C07D 239/48; A61K 31/505
USPC .......................................... 544/332; 514/275
See application file for complete search history.

(56) References Cited

U.S. PATENT DOCUMENTS

2010/0029610 A1* 2/2010 Singh et al. ............. 514/210.18

FOREIGN PATENT DOCUMENTS

| CN | 101175753 A | 5/2008 |
|---|---|---|
| CN | 101300234 A | 11/2008 |
| CN | 102083800 A | 6/2009 |
| CN | 101605766 A | 12/2009 |
| CN | WO2013/060098 A1 | 5/2013 |
| WO | WO2010/144647 A1 | 12/2010 |

OTHER PUBLICATIONS

Ten Hacken et al., Microenvironment dependency in Chronic Lymphocytic Leukemia: The basis for new targeted therapies, Pharmacology & Therapeutics, vol. 144, pp. 338-348 (2014).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1995.*
Arnold, Lee, et al; "Pyrrolo2,3-dpyrimidines Containing an Extended 5-Substituent as Potent and Selective Inhibitors of Ick I"; Bioorganic & Medicinal Chemistry Letters 10 (2000) 2167-2170.
Burchat, Andrew, et al; "Pyrazolo 3,4-dpyrimidenes Containing an Extended 3-Substituent as Potent Inhibitors of Lck—a Slectivity Insight"; Bioorganic & Medicinal Chemistry Letters 12 (2002) 1687-1690.
Dey, Pranab, et al; Combined applications of fine needle aspiration cytology and Flow cytometric immunphenotyping for diagnosis and classification of non Hodgkin Lymphoma; CytoJournal 2006, 3:24 www.cytojournal.com/content/3/1/24.
Fedorak, Richard, et al; "A Novel colon-specific steriod prodrug enhances sodium chloride absorption in rat colitis"; The American Pysiological Society; 1995 ; pp. G210-G218.
Di Paolo; Julie A, et al; Specific Btk inhibition suppresses B cell- and myeloid cell-mediated arthritis; Nature Chemical Biology; vol. 7; Jan. 2011; Published online Nov. 28, 2010; DOI: 10.1038/NCHEMBIO.481.
Honigberg, Lee A., et al; "The Bruton tyrosone kinase inhibitor PCI-32765 blocks B-cell activation and is efficacious in models of autoimmune disease and B-cell malignancy"; PNAS; Jul. 20, 2010; vol. 107, No. 29, 13075-13080; www.pnas.org/cgi/doi/10,1073/pnas.1004594107.
Nandakumar, Kutty Selva, et al; "Collagen Type II—Specific Monoclonal Antibody-Induced Arthritis in Mice"; Antibody-Mediated Arthritis; Nov. 2003; vol. 163, No. 5; pp. 1827-1837.
Nisitani, Sazuku, et al; In situ detection of activated Bruton's tyrosine kinase in the Ig signaling complex by phosphopeptide-specific monoclonal antibodies; Proc. Natl. Acad. Sci. USA; vol. 96; pp. 2221-2226, Mar. 1999; Immunology.
Pagel, John M., et al; "Induction of Apoptosis Using Inhibitors of Lysophosphatic Acid Acyltransferase- and Anti-CD20 Monoclonal Antibodies for Treatment of Human Non-Hodgkin's Lymphomas"; Clin Cancer Res 2005, 11:4857-4866.
Herman, Sarah E.M., et al; Bruton tyrosine kinase represents a promising therapeutic target for treatment of chronic lymphocytic leukemia and is effectively targeted by PCI-32766;Blood, Jun. 9, 2011; vol. 117; No. 23.
PCT/CN2012/001432; International Search Report; Feb. 7, 2013.

* cited by examiner

*Primary Examiner* — Deepak Rao
(74) *Attorney, Agent, or Firm* — Gearhart Law, LLC

(57) ABSTRACT

Disclosed is a compound of (aminophenylamino) pyrimidyl benzamides and a synthesis method thereof. The compound has Btk-inhibition activity and can be used to treat autoimmune diseases, heteroimmune diseases, cancers or thromboembolic diseases.

26 Claims, No Drawings

KINASE INHIBITOR AND METHOD FOR TREATMENT OF RELATED DISEASES

FIELD OF THE INVENTION

The present application provides the molecular structures of compounds of (aminophenylamino) pyrimidyl benzamides and synthesis methods thereof, as well as use of the compounds in inhibiting kinases and treating B-cell associated diseases.

BACKGROUND OF THE INVENTION

The kinase's action mechanism is to transfer phosphate groups from high-energy donor molecules (e.g., ATP) to specific molecules, which is a process called phosphorylation. Protein kinases alter the activities of specific proteins through phosphorylation so as to control and regulate protein-associated signal transduction and other effects on cells. Due to the importance of protein kinases in cell signaling, the selectivity of some small molecule compounds for specific kinases will be helpful for further understanding on the cell signaling process. Meanwhile, small molecule compounds control the functions of cells by modulating the activities of kinases, which makes protein kinases become good drug targets in the treatment of clinical diseases.

Bruton's tyrosine kinase (Btk), a member of the Tec family of non-receptor tyrosine kinases, plays a key role in signal transduction in hematopoietic cells (except T lymphocytes and plasma cells), especially in the B cells which play an important role in the pathogenesis of autoimmune and inflammatory diseases. Btk has shown good clinical efficacy in many serious refractory diseases, such as rheumatoid arthritis, lymphoma and leukemia.

Btk plays a critical role in the process of B-cell development, differentiation, proliferation, activation and survival. The effect of Btk on B cells is achieved by controlling B-cell receptor (BCR) signaling pathway. Btk locates at adjacent downstream of the BCR. Btk passes down the signal upon BCR stimulation, and after a series of signal transduction, finally leading to intracellular calcium mobilization and protein kinase C activation. X-linked agammaglobulinemia (also called Bruton's syndrome, XLA) is a rare genetic disease. These XLA patients are unable to produce mature B cells. Normal B cells resist external infection by producing antibodies (called immunoglobulins). Due to the lack of B cells and antibodies, XLA patients are easy to obtain serious or even fatal infections. Further researches found that the direct reason that inhibits B-cell development is gene mutation of Btk. Thus it is proved that Btk plays an extremely important role in the development and function of normal B cells.

Btk becomes a remarkable drug target in cancers that are relevant to the B-cell, especially the B-cell lymphoma and leukemia.

Cells need BCR signals to grow and proliferate. Since Btk is an indispensable key member in the BCR signaling pathway, Btk inhibitors can block BCR signaling and induce apoptosis of cancer cells. Currently, there are two Btk inhibitors in the United States and Europe for clinical treatment of chronic lymphocytic leukemia (Cll) and small lymphocytic lymphoma (Sll): PCI-32765 (clinical phase III) and AVL-292 (clinical phase I). (See S E Herman et al. (2011), Blood 117 (23): 6287-96). Btk is also associated with acute lymphoblastic leukemia. Acute lymphoblastic leukemia is the most common cancer in children, and has a poor prognosis in adult patients. Genetic analysis found that the deficiency of BTK expression was found in all types of leukemia. Defective Btk protects leukemia cells from apoptosis.

Btk is also a therapeutic target for autoimmune diseases. Rheumatoid arthritis is a chronic autoimmune disease. Btk is an important component of BCR signaling in B cells and FC-γ signaling in bone marrow cells. Btk inhibitors are expected to reduce two main components of autoimmune diseases: pathogenic auto-antibodies produced by B cells and pro-inflammatory cytokine produced by myeloid cells. In cell experiments, it is proved that Btk inhibitors can effectively reduce auto-antibodies and pro-inflammatory cytokines. In mice with collagen-induced arthritis, Btk inhibitors reduced in vivo level of auto-antibodies and effectively controlled the disease. These results provide a new understanding of Btk functions during the development of B-cells or bone-marrow-cells driven diseases, and provide a convincing reason for targeting Btk in the treatment of rheumatoid arthritis. (See L A Honigberg et al. (2010), Proc Natl Acad Sci USA 107 (29): 13075-80. J A Di Paolo et al. (2011), Nat Chem Biol 7 (1): 41-50.)

The role of Btk in inflammatory diseases has been demonstrated by a rat basophilic leukemia cells (RBL-2H3) model. RBL-2H3 is a common model for mast cell inflammatory diseases research. Mast cells are rich of basophilic granules, and play a leading role in immunoglobulin E (IgE)-mediated allergic reactions. Small interfering RNA (siRNA), and LFM-A13 (an effective Btk inhibitor) can suppress the mast cell induced inflammatory response by inhibiting Btk activity. In the mast cells treated with siRNA and LFM-A13, the release of a pro-inflammatory mediator, histamine, is reduced by 20-25%.

It is also reported in literatures that Btk is used as a therapeutic target in heteroimmune diseases and thromboembolic diseases.

Therefore, the present disclosure aims to provide a novel compound for treating autoimmune diseases, heteroimmune diseases, inflammatory diseases, cancers, or thromboembolic diseases.

SUMMARY OF THE INVENTION

In one aspect of the present disclosure, it provides:

A compound of formula (I),

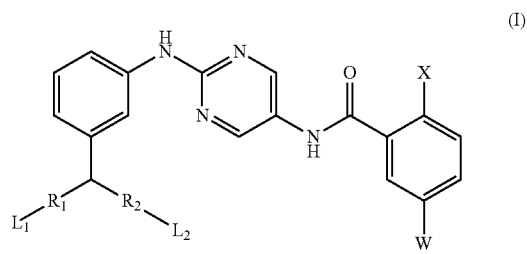

or pharmaceutically acceptable salts thereof, wherein:

W is selected from H, $C_{1-6}$ alkyl, —(NH—CO)$_n$-L-L$_3$, —(CO—NH)$_n$-L-L$_3$, and —(NH—CO)$_n$—NH-L-L$_3$;

wherein:
L is a bond, $C_{1-3}$ alkylene or $C_{2-3}$ alkenylene;
$L_3$ is $C_{3-8}$ cycloalkyl, such as Aryl such as phenyl, naphthyl, phenanthryl, anthryl, fluorenyl, and indenyl, or heteroaryl such as The $C_{3-8}$ cycloalkyl, aryl and heteroaryl is optionally substituted with 1, 2 or 3 substituents selected from the group consisting of halogen such as F and Cl, amino, $C_{1-6}$ alkyl, $C_{1-6}$ alkoxyl, halo-$C_{1-6}$ alkyl such as perhalo-$C_{1-6}$ alkyl such as $CF_3$;

n is an integer of 0 or 1;

X is selected from H, halogen such as F and Cl, and $C_{1-6}$ alkyl such as methyl;

$R_1$ and $R_2$, same or different from each other, are each independently selected from H, C(O) and $S(O)_2$;

$L_1$ and $L_2$, same or different from each other, are each independently selected from $C_{2-3}$ alkenyl optionally substituted with $C_{1-3}$ alkyl, and $C_{1-3}$ alkyl-NHC(O)—$C_{2-3}$ alkenyl;

with the provisos that when $R_1$ is H, $L_1$ is not present; and when $R_2$ is H, $L_2$ is not present.

In a preferred embodiment,

W is selected from H, ethyl, —(NH—CO)$_n$-L-$L_3$, —(CO—NH)$_n$-L-$L_3$, and —(NH—CO)$_n$—NH-L-$L_3$, wherein:
L is a bond or vinylene;
$L_3$ is cyclopropyl, phenyl, naphthyl, isoxazolyl or benzo[d][1,3]dioxole group optionally substituted with 1 or 2 substituents selected from F, Cl, amino, methoxyl and $CF_3$;

n is an integer of 1.

In another preferred embodiment,
X is selected from H, F, Cl, and methyl.

In another preferred embodiment,
$R_1$ and $R_2$, same or different from each other, are each independently selected from H, C(O) and $S(O)_2$;

$L_1$ and $L_2$, same or different from each other, are each independently selected from $C_{2-3}$ alkenyl, and methyl-NHC(O)-ethenyl;

with the provisos that when $R_1$ is H, $L_1$ is not present; and when $R_2$ is H, $L_2$ is not present.

In another preferred embodiment,
W is selected from H, ethyl, —(NH—CO)$_n$-L-$L_3$, —(CO—NH)$_n$-L-$L_3$, and —(NH—CO)$_n$—NH-L-$L_3$, wherein:
L is a bond or vinylene;
$L_3$ is cyclopropyl, phenyl, naphthyl, isoxazolyl or benzol[d][1,3]dioxole group optionally substituted with 1 or 2 substituents selected from F, Cl, amino, methoxyl and $CF_3$;

n is an integer of 1;
X is selected from H, F, Cl, and methyl;
$R_1$ and $R_2$, same or different from each other, are each independently selected from H, C(O) and $S(O)_2$;

$L_1$ and $L_2$, same or different from each other, are each independently selected from $C_{2-3}$ alkenyl, and methyl —NHC(O)-ethenyl;

with the provisos that when $R_1$ is H, $L_1$ is not present; and when $R_2$ is H, $L_2$ is not present. In another aspect of the present disclosure, it provides a compound selected from:

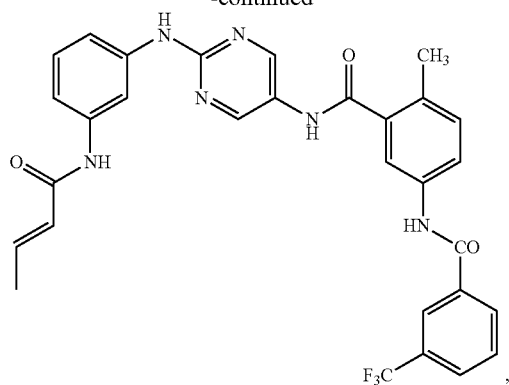
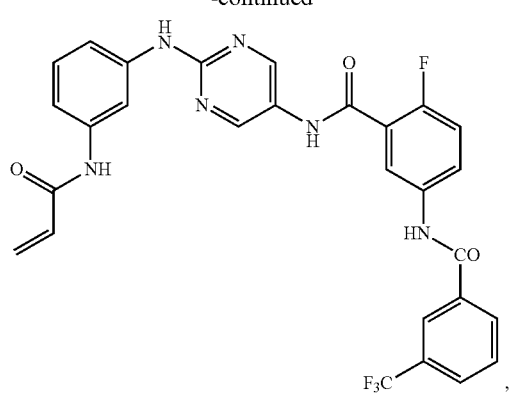
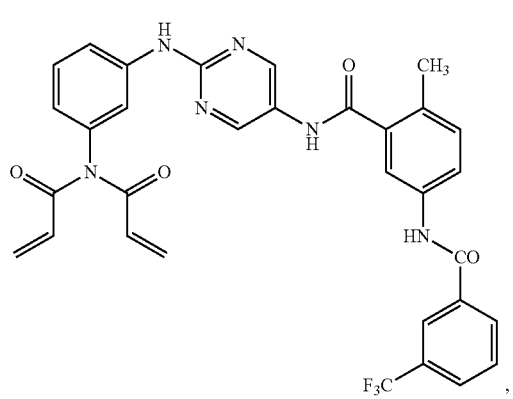
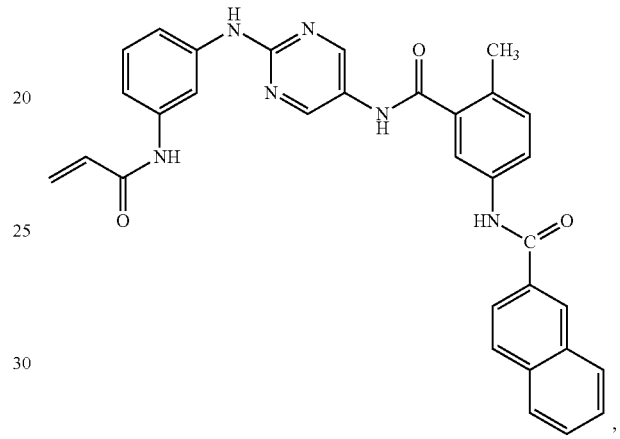
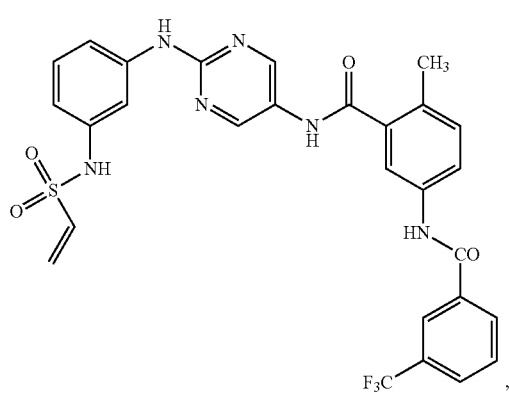
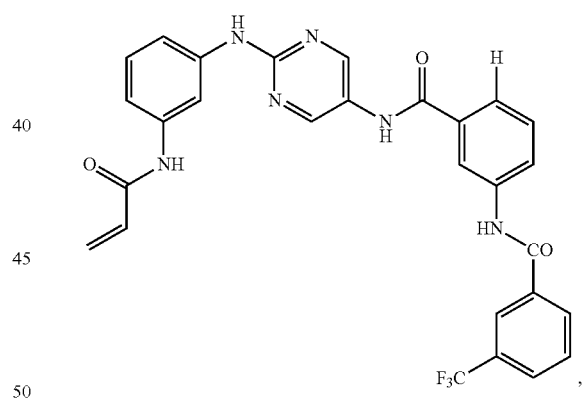
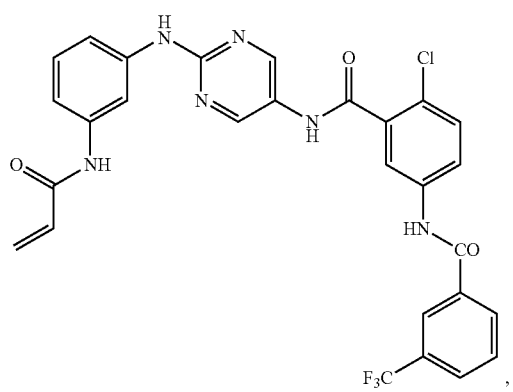
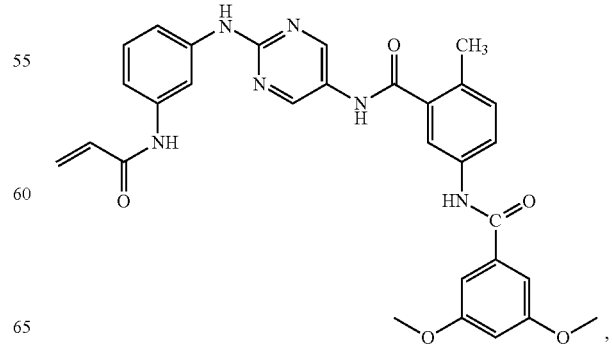

7
-continued
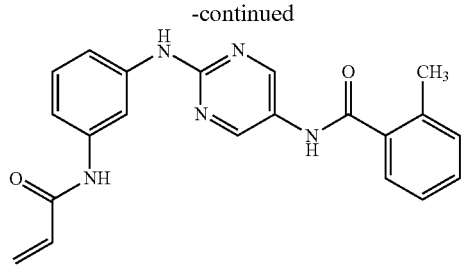
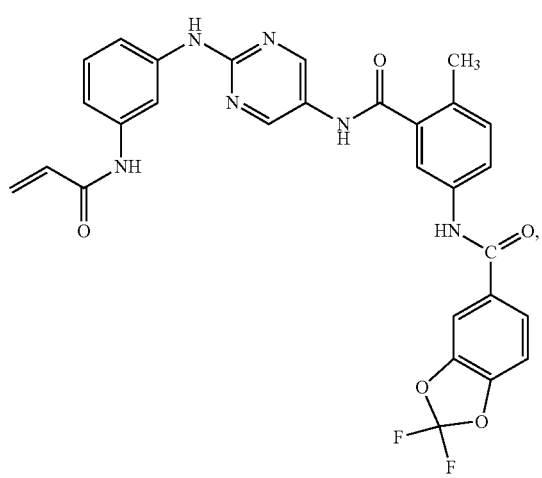
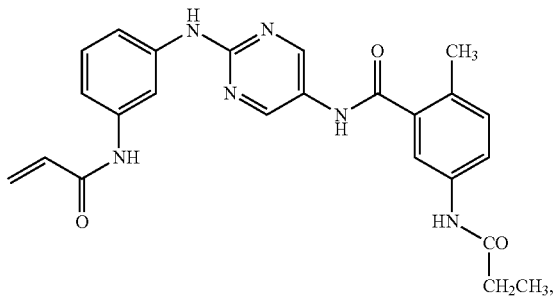
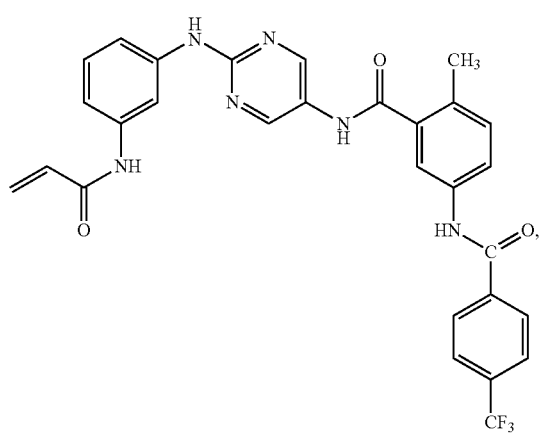
8
-continued
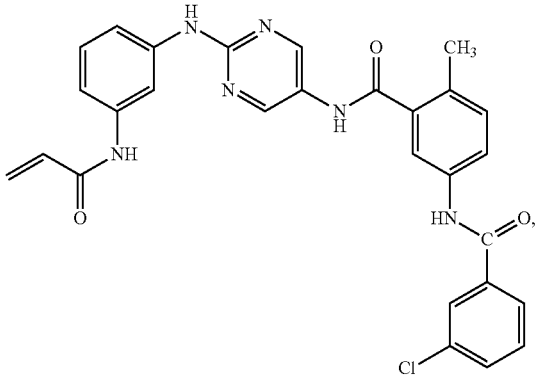
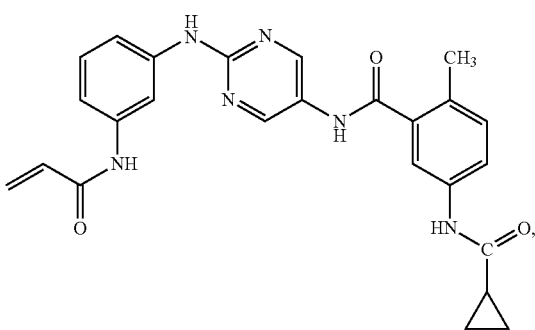
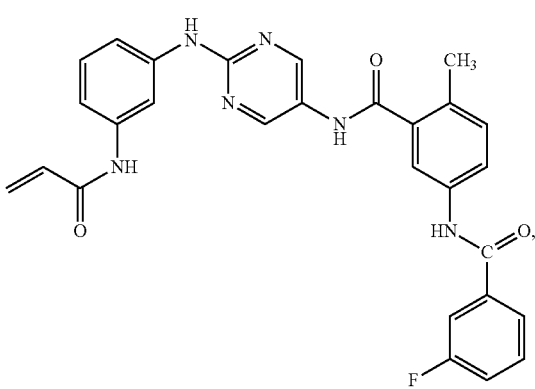
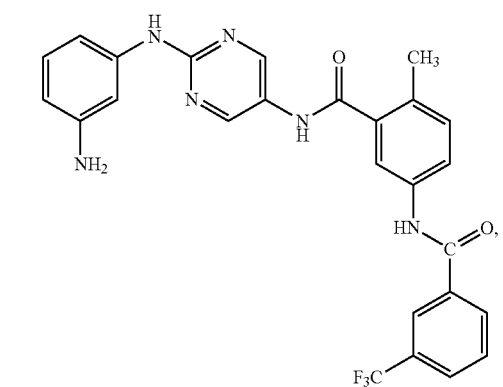

-continued
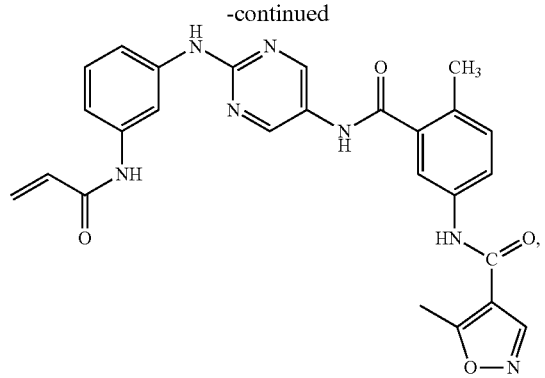
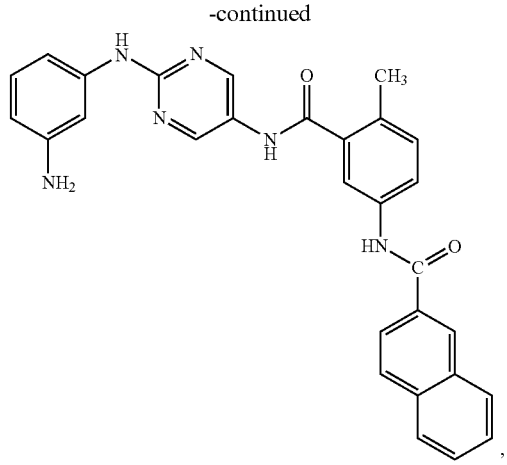
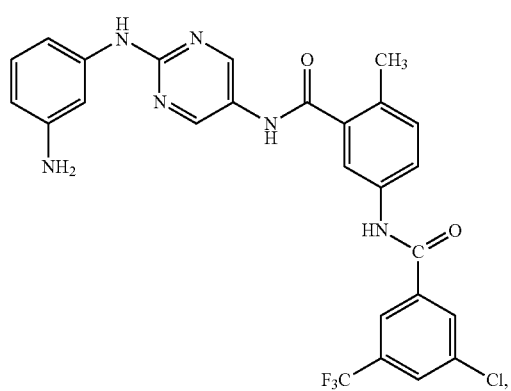
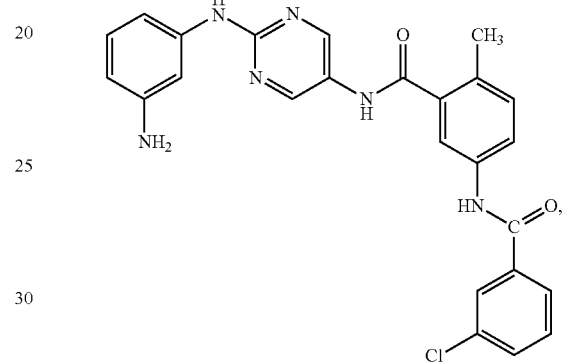
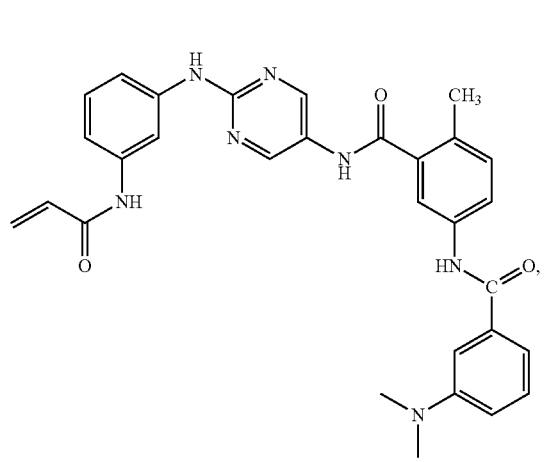
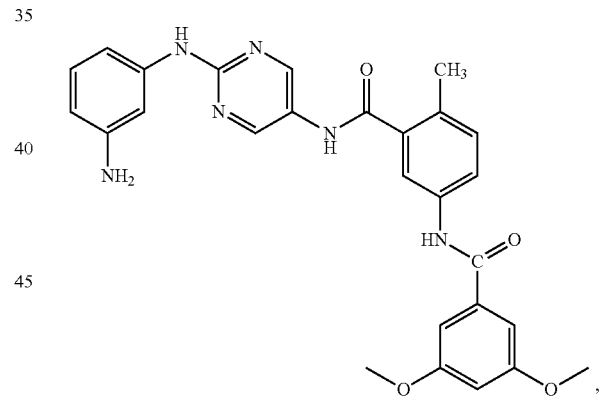
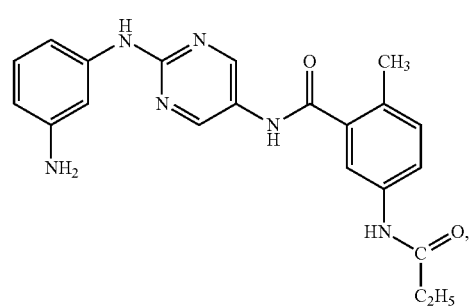
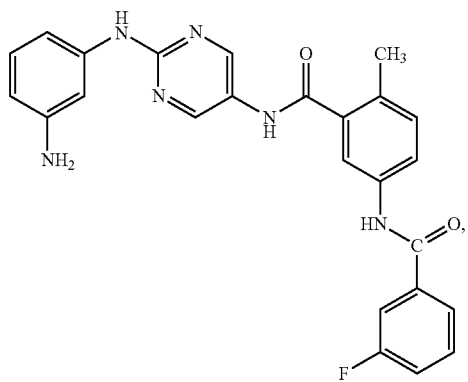

11
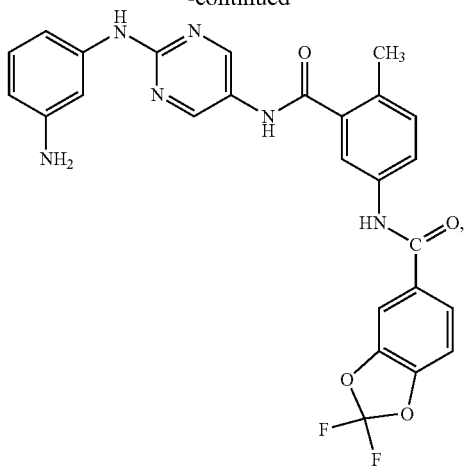
12
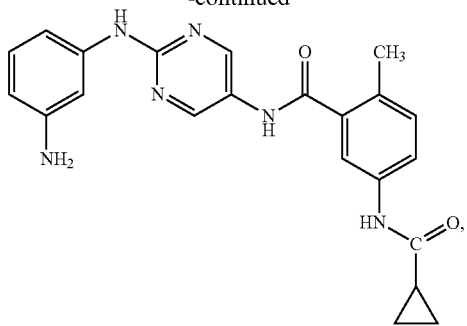
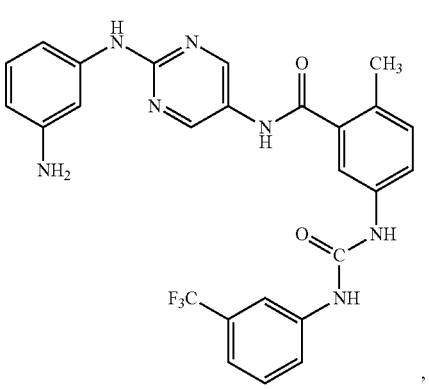
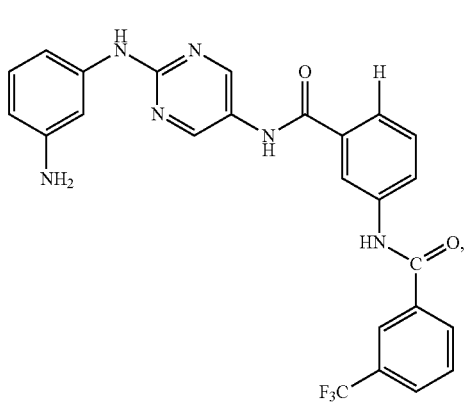
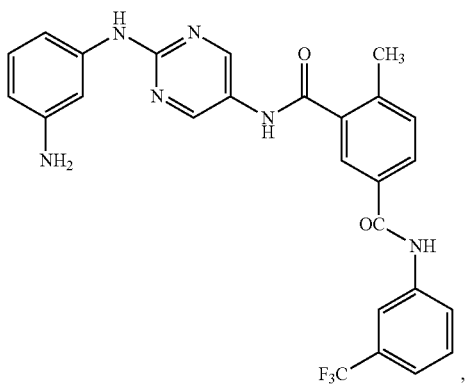

-continued

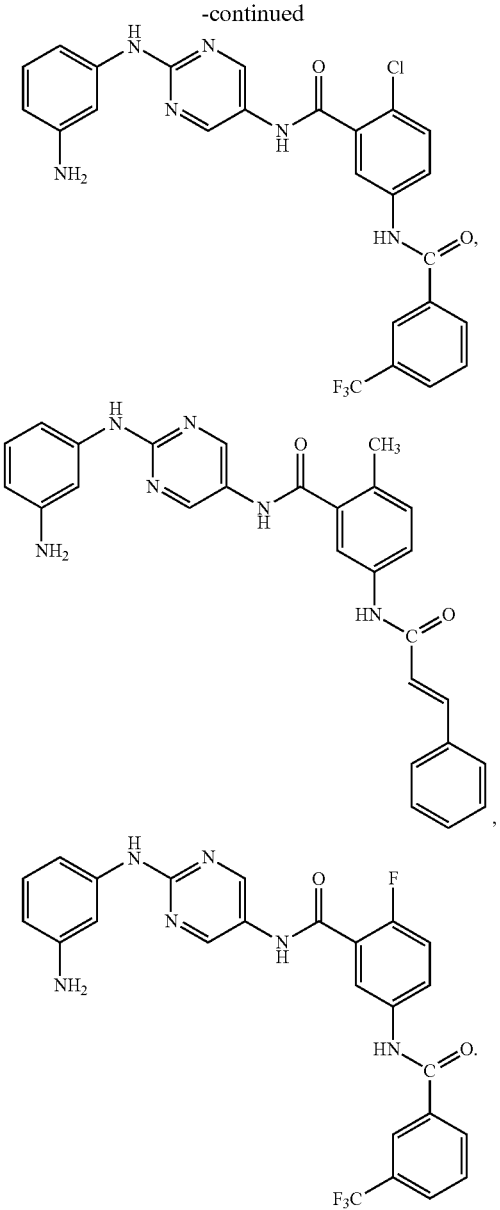

In another aspect of the present disclosure, it provides pharmaceutical compositions comprising a therapeutically effective amount of the compound of the present invention and pharmaceutically acceptable excipients.

In another aspect of the present disclosure, it provides uses of the compounds or the compositions of the present invention in the manufacture of medicaments for treating the following diseases or conditions: autoimmune diseases, heteroimmune diseases, inflammatory diseases, cancers or thromboembolic diseases.

In another aspect of the present disclosure, it provides the compounds or the compositions of the present invention used in methods for treating the diseases or conditions as follows: autoimmune diseases, heteroimmune diseases, inflammatory diseases, cancers or thromboembolic diseases.

In another aspect of the present disclosure, it provides methods for treating diseases or conditions as follows: autoimmune diseases, heteroimmune diseases, inflammatory diseases, cancers or thromboembolic diseases, said methods comprising administering the compounds or the compositions of the present invention to subjects in need thereof, e.g. a mammal such as human.

For any and all of the embodiments, substituents can be selected from a subset of the listed alternatives. For example, in some embodiments, W is selected from H, ethyl, —(NH—CO)$_n$-L-L$_3$, —(CO—NH)$_n$-L-L$_3$, and —(NH—CO)$_n$—NH-L-L$_3$. In some further embodiments, W is selected from —(NH—CO)$_n$-L-L$_3$, —(CO—NH)$_n$-L-L$_3$, and —(NH—CO)$_n$—NH-L-L$_3$. In some further embodiments, W is selected from —(NH—CO)$_n$-L-L$_3$.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

EMBODIMENTS

Unless defined otherwise, all technical and scientific terms used herein have the same meaning as they are commonly understood by one skilled in the art to which the claimed subject matter belongs.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York.

"$C_{1-6}$ alkyl" refers to an alkyl group with 1 to 6 carbon atoms, including methyl, ethyl, propyl, butyl, pentyl and hexyl, and all the possible isomeric forms thereof, e.g., n-propyl and isopropyl, n-butyl, isobutyl, sec-butyl and tert-butyl, and the like. "$C_{1-6}$ alkyl" includes all sub-ranges contained therein, e.g. $C_{1-2}$ alkyl, $C_{1-3}$ alkyl, $C_{1-4}$ alkyl, $C_{1-5}$ alkyl, $C_{2-5}$ alkyl, $C_{3-5}$ alkyl, $C_{4-5}$ alkyl, $C_{3-4}$ alkyl, $C_{3-5}$ alkyl and $C_{4-5}$ alkyl.

"$C_{1-3}$ alkylene" includes methylene, ethylidene, propylidene and isopropylidene.

"$C_{2-3}$ alkenyl" includes ethenyl (—CH=CH$_2$), propenyl (—CH=CHCH$_3$) and isopropenyl (—C(CH$_3$)=CH$_2$).

"$C_{2-3}$ alkenylene" includes ethenylene (—CH=CH—), propenylene (—CH=CHCH$_2$—) and isopropenylene (—C(CH$_3$)=CH—).

The term "aromatic group" refers to a planar ring having a delocalized membered π-electron system containing 4n+2π electrons, where n is an integer. Aromatic groups can be formed from five, six, seven, eight, nine or more than nine atoms. Aromatic groups can be optionally substituted. Aromatic groups include "aryl" (each of the atoms forming the ring is a carbon atom), and "heteroaryl" (the atoms forming the ring include carbon atom(s) and heteroatom(s) selected from such as oxygen, sulfur and nitrogen). "Aryl" and "heteroaryl" include monocyclic or fused-ring polycyclic (i.e., rings which share adjacent pairs of ring atoms) groups.

Examples of aryl groups include, but are not limited to phenyl, naphthalenyl, phenanthrenyl, anthracenyl, fluorenyl and indenyl.

Examples of heteroaryl groups include,

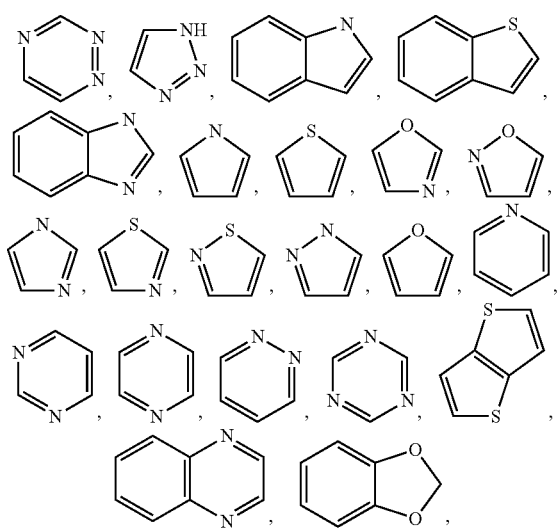

"C$_{3-8}$ cycloalkyl" refers to a non-aromatic monocyclic or polycyclic radical that contains only carbon and hydrogen, having 3 to 8 carbons forming a ring, and may be saturated, partially unsaturated, or fully unsaturated. Examples of C$_{3-8}$ cycloalkyl groups include the following:

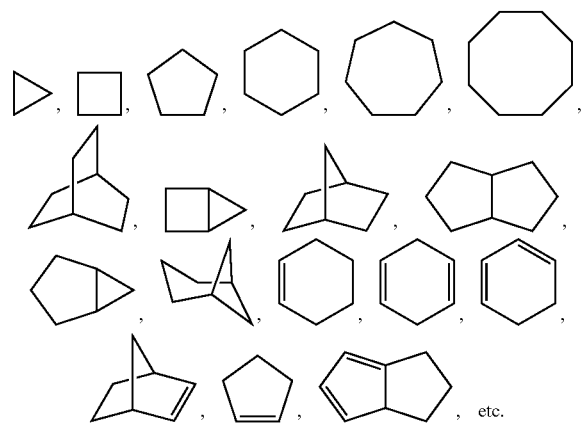

"Halogen" refers to fluoro, chloro, bromo and iodo.

"C$_{1-6}$ alkoxyl" refers to the group (C$_{1-6}$ alkyl)O—, wherein the C$_{1-6}$ alkyl is as defined herein.

"Halo-C$_{1-6}$ alkyl" refers to halo-(C$_{1-6}$ alkyl)-, wherein the C$_{1-6}$ alkyl is as defined herein. Halo-C$_{1-6}$ alkyl includes perhalogenated C$_{1-6}$ alkyl, wherein all the hydrogen atoms in C$_{1-6}$ alkyl are replaced with halogen, such as —CF$_3$, —CH$_2$CF$_3$, —CF$_2$CF$_3$, —CH$_2$CH$_2$CF$_3$ and the like.

"C$_{2-3}$ alkenyl optionally substituted with C$_{1-3}$ alkyl" refers to a C$_{2-3}$ alkenyl or a C$_{2-3}$ alkenyl substituted with C$_{1-3}$ alkyl, wherein it connects to the main structure of the compound through C$_{2-3}$ alkenyl.

"C$_{1-3}$ alkyl-NHC(O)—C$_{2-3}$ alkenyl" refers to C$_{2-3}$ alkenyl substituted with C$_{1-3}$ alkyl-NHC(O), wherein it connects to the main structure of the compound through C$_{2-3}$ alkenyl.

The term "bond" refers to a chemical bond between two atoms, or two moieties when the atoms joined by the bond are considered to be part of larger substructure.

The term "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP 000052).

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "inhibits", "inhibiting" or "inhibitor" of a kinase, as used herein, refer to inhibition of enzymatic phosphotransferase activity.

Autoimmune diseases, as disclosed herein, include but are not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

Heteroimmune diseases, as disclosed herein, include but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Inflammatory diseases, as disclosed herein, include but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

Cancers, as disclosed herein, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

Thromboembolic disorders, as disclosed herein, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions are known in the art. See, e.g., *Harrison's Principles of Internal Medicine©*," 16$^{th}$ ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of irreversible Btk inhibitor compounds for treating any of the foregoing diseases.

For example, dosing of irreversible Btk inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), Am. J. Pathol 163:1827-1837.

In another example, dosing of irreversible Btk inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13): 4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an irreversible Btk inhibitor. Cellular assays known in the art can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to a subject can be increased or decreased as needed so as to maintain a level of Btk inhibition optimal for treating the subject's disease state.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared using the synthetic methods described herein as a single isomer or a mixture of isomers.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds in unoxidized form can be prepared from N-oxides by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), *The Organic Chemistry of Drug Design and Drug Action*, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol, 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Synthesis of Compounds

Synthetic Scheme I

Step 1:

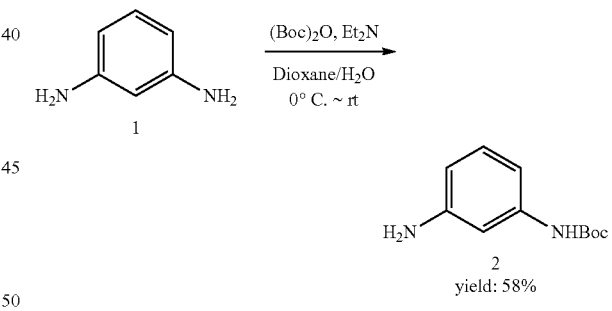

m-phenylenediamine (0.500 g, 4.62 mmol), (Boc)$_2$O (0.92 mL, 4.02 mmol) and triethylamine (1.4 mL, 9.98 mmol) were added to a mixed solvent system of 1,4-dioxane and water (30 mL, 2:1 V/V) that has been cooled to 0° C. After stirring for 1 hour at 0° C., the reaction system was recovered to room temperature and stirred for another 10 hours. The reaction solution was concentrated under reduced pressure to yield yellow oil, which was dissolved in ethyl acetate, washed with saturated sodium bicarbonate solution and then with saturated brine. The final organic phase was dried with magnesium sulfate, filtered, and concentrated under reduced pressure. The concentrate was purified with silica gel column chromatography (n-hexane:ethyl acetate=10:1~8:1~4:1~2:1~1:1) to give Compound 2 (0.48 g, yield: 58%) as a white solid.

Step 2:

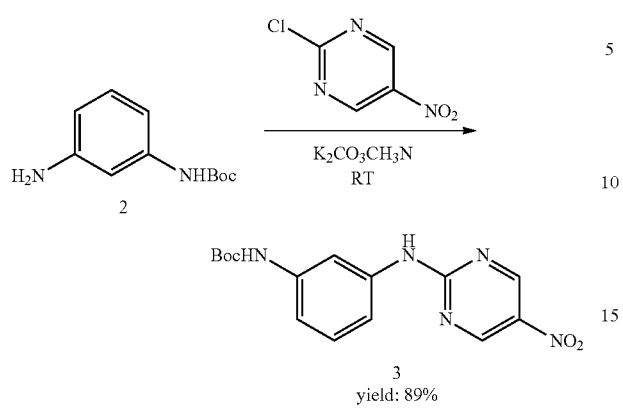

3
yield: 89%

Compound 2 (0.352 g, 1.69 mmol) and 2-chloro-5-nitro-pyrimidine (0.270 g, 1.69 mmol) were firstly dissolved in 12 mL acetonitrile, and then potassium carbonate (0.702 g, 5.08 mmol) was added to the solution. The whole reaction system was stirred for 3 hours at room temperature, and then the reaction solvent was removed by rotary evaporation under reduced pressure. The concentrated substance was then dissolved in ethyl acetate, washed with water and then with saturated brine. The final organic phase was dried with sodium sulfate, concentrated under reduced pressure and purified by silica gel column chromatography (hexane:ethyl acetate=4:1~3:1~2:1~1:1~1:3) to give Product 3 (0.50 g, yield: 89%) as a yellow solid.

Step 3:

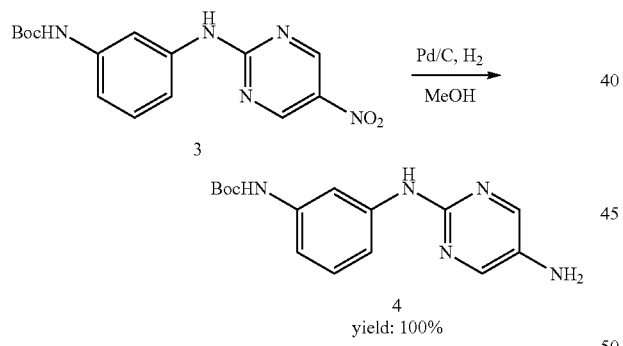

4
yield: 100%

Compound 3 (0.500 g, 1.51 mmol) and palladium-carbon (0.16 g, mass fraction: 5%) were added to a 25 ml two-necked flask, 10 mL methanol was added to the reaction system with slow stirring. After replacing the air in the whole reaction system with nitrogen, a hydrogen-filled balloon with sufficient hydrogen was connected to the system, and then the nitrogen in the reaction system was replaced with hydrogen in the balloon (three times). The reaction system was stirred for 3 hours at room temperature before terminating the reaction. The reaction solution was filtered with frit funnel to remove the palladium-carbon residue and result in a brown filtrate. The filtrate was concentrated and purified with silica gel column chromatography (n-hexane:ethyl acetate=1:1~1:2~1:4~1:6) to give Product 4 (0.45 g, yield: 100%) as a yellow solid.

Step 4:

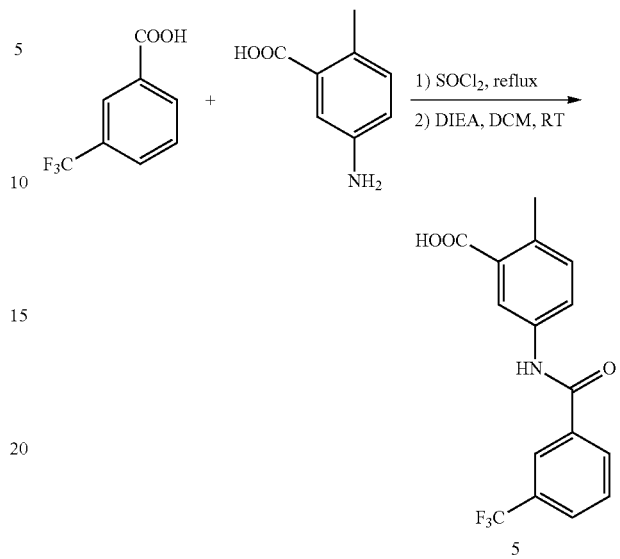

3-(trifluoromethyl)benzoic acid (0.500 g, 2.63 mmol) was dispersed in 5 mL thionyl chloride. The reaction system was heated to 80° C. and maintained under stirring and refluxing for 1 hour, then cooled to room temperature. 10 mL toluene was added to the reaction liquid with slow stirring, and then the reaction solution was concentrated by rotary evaporation under reduced pressure to yield light yellow oil. The concentrated substance was dissolved in 15 ml methylene chloride, and then 5-amino-2-methyl-benzoic acid (0.478 g, 3.16 mmol) and diisopropylethylamine (0.1 mL) were added to this solution. The reaction system was stirred overnight at room temperature to precipitate a large amount of white solid. The reaction solution was concentrated under reduced pressure and dispersed in ethyl acetate, washed with saturated ammonium chloride solution and then with saturated brine. The final organic phase was dried with anhydrous sodium sulfate, concentrated under reduced pressure, and purified by silica gel column chromatography to give Product 5 (0.68 g, yield: 80%) as a white solid.

Step 5:

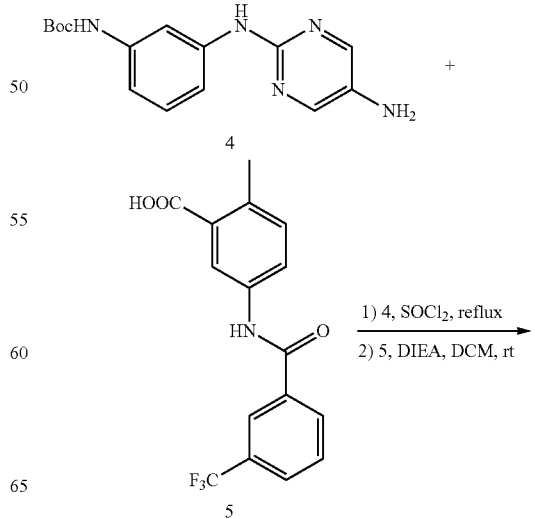

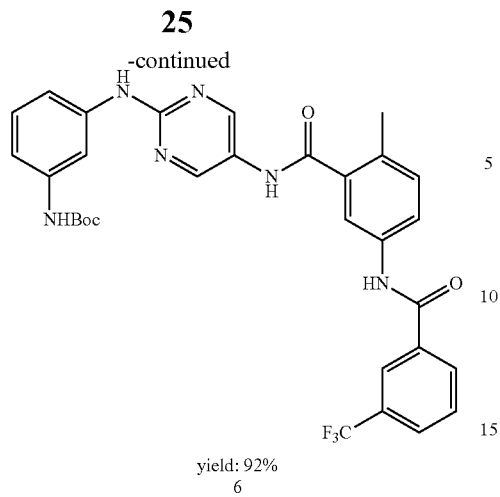

yield: 92%

6

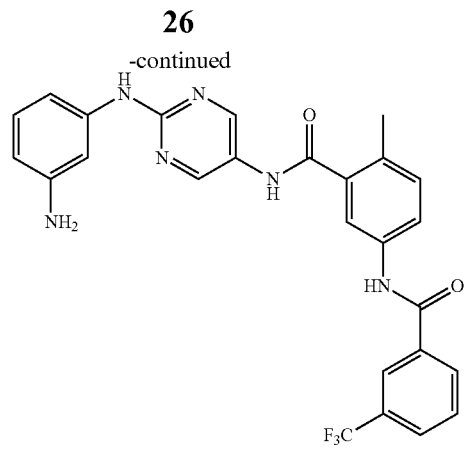

7

Compound 4 (0.263 g, 0.813 mmol) was dispersed in 3 mL thionyl chloride. The reaction system was heated to 80° C. and maintained under stirring and refluxing for 1 hour, then cooled to room temperature. 5 mL toluene was added to the reaction solution with slow stirring, and the reaction solution was concentrated under reduced pressure to yield brown oil. The concentrated substance was dissolved in 5 mL dichloromethane, then Compound 5 (0.270 g, 0.894 mmol) and diisopropylethylamine amine (0.1 mL) were added. The final reaction system was stirred overnight at room temperature, and the reaction solution was concentrated to solid under reduced pressure. The residue was dissolved in ethyl acetate, washed with saturated sodium bicarbonate solution and then with saturated brine. The final organic phase was dried with anhydrous magnesium sulfate and concentrated under reduced pressure, the concentrated substance was purified by silica gel column chromatography (n-hexane/ethyl acetate=2:1~1:1~1:2~1:4) to give Compound 6 (0.451 g, yield: 92%) as a yellow solid.

Step 6:

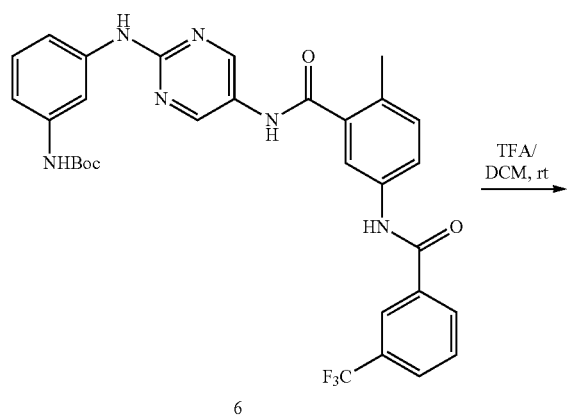

6

Compound 6 (0.278 g, 0.458 mmol) was dispersed in 2 mL dichloromethane. 2 mL trifluoroacetic acid was dropped into the reaction system slowly under stirring. The final reaction system was stirred for 1 hour at room temperature, and then was concentrated under reduced pressure to yield a solid. The residue was dissolved in ethyl acetate, washed with 10% sodium hydroxide solution and then with saturated brine. The final organic phase was dried with anhydrous magnesium sulfate and concentrated under reduced pressure. The concentrated substance was purified by silica gel column chromatography (n-hexane/ethyl acetate=1:1~1:2~1:4) to give Product 7 (0.193 g, yield: 83%) as a white solid.

Synthetic Scheme II

Step 1:

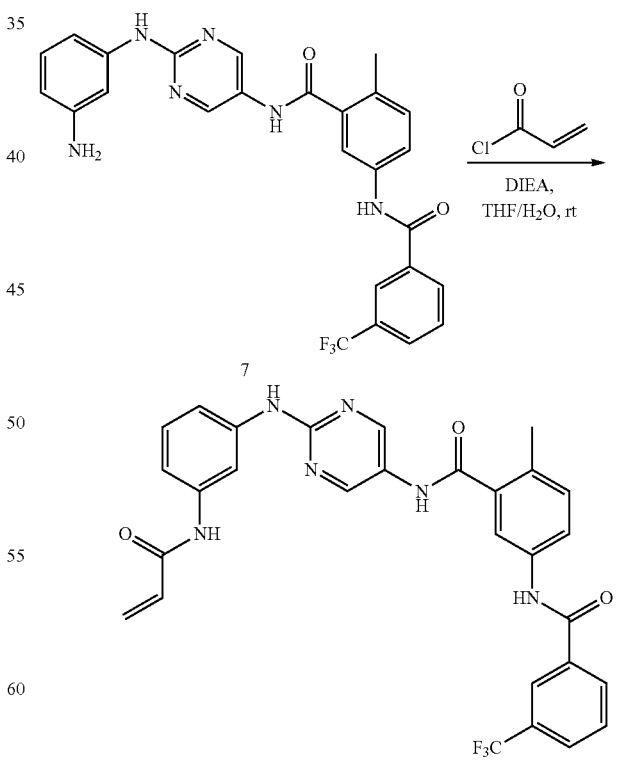

Compound 7 (0.080 g, 0.16 mmol) was dispersed in a mixed solvent of THF and water (4 mL, 1:1 V/V), and then diisopropylethylamine (27 μL, 0.16 mmol) was added. Acryloyl chloride (13 μL, 0.16 mmol) was dropped into the reaction system slowly under stirring. The reaction solution was stirred at room temperature for 2 hours, and then concentrated under reduced pressure. The residue was dissolved with ethyl acetate, washed with 10% citric acid solution and then with saturated brine. The final organic phase was dried with anhydrous magnesium sulfate and concentrated under reduced pressure. The concentrated substance was purified by silica gel column chromatography (n-hexane/ethyl acetate=1:1~1:2) to give Product 8 (80 mg, yield: 89%) as a white powered solid.

Synthetic Scheme III
Step 1:

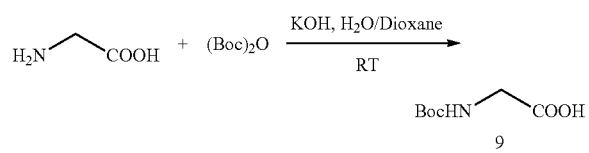

Glycine (1.00 g, 13.3 mmol) was dissolved in a mixed solvent of potassium hydroxide aqueous solution and 1,4-dioxane (40 mL, 1:1 V/V). (Boc)$_2$O (3.7 mL, 16.0 mmol) was added to the reaction solution. The reaction system was stirred for 12 hours at room temperature, and then the reaction solution was concentrated under reduced pressure. The concentrate was dissolved in ethyl acetate, washed with 10% sodium bisulfate solution and then with saturated brine. The final organic phase was dried with anhydrous sodium sulfate and concentrated under reduced pressure to give crude Product 9 (2.33 g, yield: 100%) as an off-white solid.

Step 2:

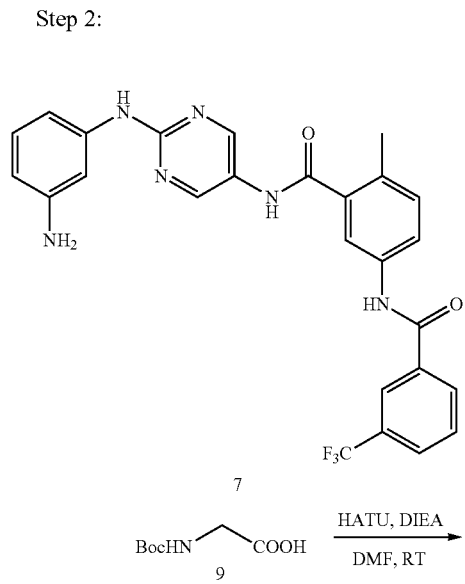

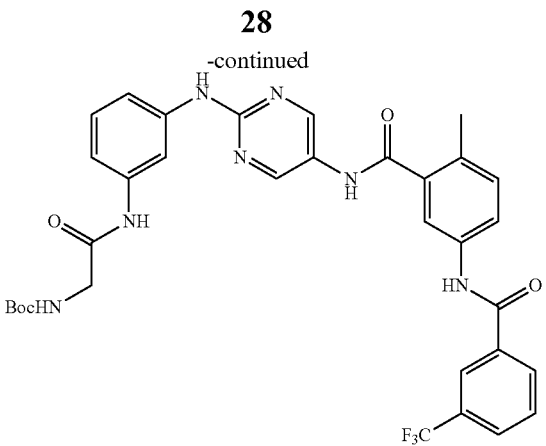

Compound 7 (0.090 g, 0.177 mmol), Boc-protected glycine 9 (0.032 g, 0.213 mmol) and HATU (0.101 g, 0.266 mmol) were dissolved in 3 mL DMF, diisopropylethylamine (44 μL, 0.266 mmol) was slowly added under stirring. The reaction solution was stirred for 2 hours at room temperature, and then the solvent was removed by rotary evaporation under reduced pressure. The residue was dissolved in ethyl acetate, washed with saturated sodium bicarbonate solution and then with saturated brine. The final organic phase was dried with anhydrous magnesium sulfate, filtered, concentrated under reduced pressure, and purified by silica gel column chromatography (n-hexane:ethyl acetate=1:1~1:2~1:4) to give Product 10 (0.106 g yield: 90%) as a white solid.

Step 3:

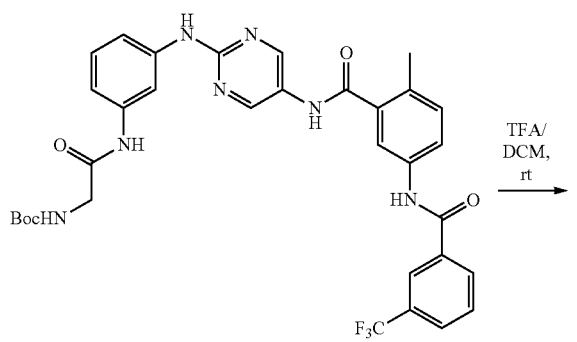

Compound 10 (0.102 g, 0.154 mmol) was dispersed in 2 mL dichloromethane. 2 mL trifluoroacetic acid was dropped into the reaction system slowly under stirring. The final reaction system was stirred for 1 hour at room temperature, and then was concentrated under reduced pressure to yield a solid. The residue was dissolved with ethyl acetate, washed with 10% sodium hydroxide solution and then with saturated brine. The final organic phase was dried with anhydrous magnesium sulfate, concentrated under reduced pressure, and dried in vacuum overnight to give Product 11 (0.080 g, yield: 92%) as a white solid.

Step 4:

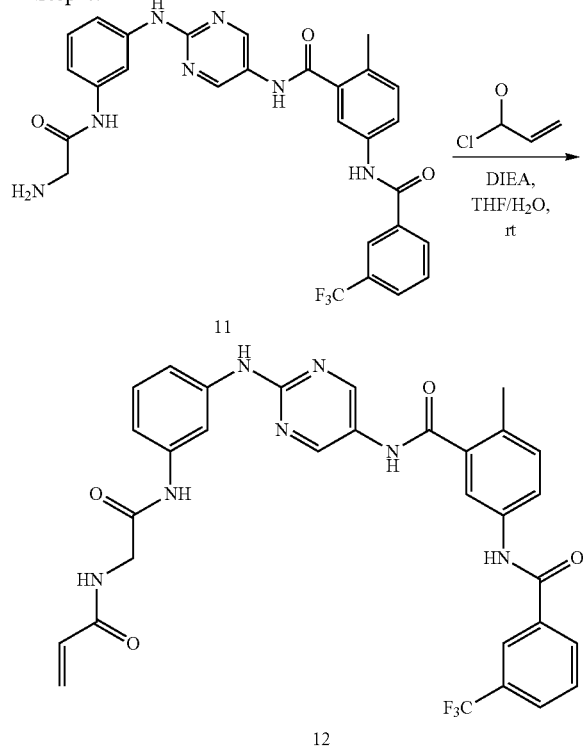

Compound 11 (0.050 g, 0.089 mmol) was dispersed in a mixed solvent of THF and water (2 mL, 1:1 V/V), and then diisopropylethylamine (18 µL, 0.11 mmol) was added. Acryloyl chloride (14 µL, 0.18 mmol) was dropped into the reaction system slowly under stirring. The reaction was stirred for 2 hours at room temperature, and then was concentrated under reduced pressure. The residue was dissolved in ethyl acetate, washed with saturated sodium bicarbonate solution and then with saturated brine. The final organic phase was dried with anhydrous magnesium sulfate and concentrated under reduced pressure. The concentrate was purified by silica gel column chromatography (hexane:ethyl acetate=1: 2~1:4~1:8~100% EA) to give Product 12 (43 mg, yield: 79%) as a white solid.

Analysis of Btk In Vitro Inhibitory Activity

The Btk $IC_{50}$ of compounds disclosed herein was determined in an acellular kinase assay by the methods or similar methods as described below.

Btk kinase activity was determined using a time-resolved fluorescence resonance energy transfer (TR-FRET) methodology. Measurements were performed in a reaction volume of 50 µL using 96-well assay plates. Kinase enzyme, inhibitor, ATP (at the Km for the kinase), and 1 µM peptide substrate (Biotin-AVLESEEELYSSARQ-$NH_2$) were incubated in a reaction buffer composed of 20 mM Tris, 50 mM NaCl, $MgCl_2$ (5-25 mM depending on the kinase), $MnCl_2$ (0-10 mM), 1 mM DTT, 0.1 mM EDTA, 0.01% bovine serum albumin, 0.005% Tween-20, and 10% DMSO at pH 7.4 for one hour. The reaction was quenched by the addition of 1.2 equivalents of EDTA (relative to divalent cation) in 25 µL of 1× Lance buffer (Perkin-Elmer). Streptavidin-APC (Perkin-Elmer) and Eu-labeled p-Tyr100 antibody (Perkin-Elmer) in 1× Lance buffer were added in a 25 µL volume to give final concentrations of 100 nM and 2.5 nM, respectively, and the mixture was allowed to incubate for one hour. The TR-FRET signal was measured on a multimode plate reader with an excitation wavelength ($\lambda_{Ex}$) of 330 nm and detection wavelengths ($\lambda_{Em}$) of 615 and 665 nm. Activity was determined by the ratio of the fluorescence at 665 nm to that at 615 nm. For each compound, enzyme activity was measured at various concentrations of compound. Negative control reactions were performed in the absence of inhibitor in replicates of six, and two no-enzyme controls were used to determine baseline fluorescence levels. IC50s were obtained using the program Batch $K_i$ (Kuzmic et al. (2000), Anal. Biochem. 286:45-50).

According to the synthetic schemes I, II and III described above, the example compounds 1-37 of the present invention were synthesized. The specific synthetic steps and characterization of the example compounds were shown in the following table. During the analysis of Btk in vitro inhibitory activity, the $IC_{50}$ values of example compounds 1-37 of the present invention was measured. In addition, the $IC_{50}$ values are given in the following table in the type of $IC_{50}$ value ranges, wherein "+++" represents $IC_{50}$<100 nM; "++" represents 100 nM<$IC_{50}$<1000 nM; "+" represents 1000 nM<$IC_{50}$<10000 nM.

TABLE 1

Synthesis of the compounds of Examples and Btk $IC_{50}$ values

| Example | Structure | Synthetic Scheme | Structure Data | Efficacy |
|---|---|---|---|---|
| 1 | 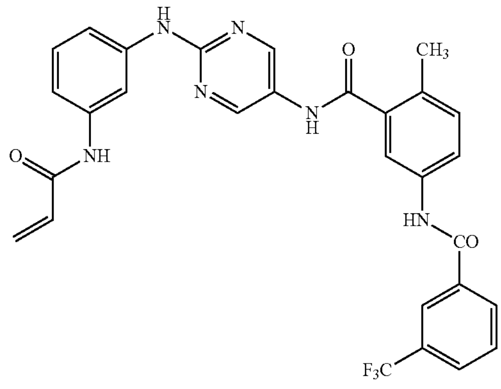 [SMILES: C=CC(=O)Nc1cccc(Nc2ncc(NC(=O)c3cc(NC(=O)c4cccc(C(F)(F)F)c4)ccc3C)cn2)c1] | Synthesized according to Synthetic Scheme II | HRMS (ESI) m/z calculated for $C_{29}H_{24}F_3N_6O_3$ (M + H)$^+$: 561.1862, found: 561.1859 | +++ |

TABLE 1-continued

Synthesis of the compounds of Examples and Btk IC$_{50}$ values

| Example | Structure | Synthetic Scheme | Structure Data | Efficacy |
|---|---|---|---|---|
| 2 | 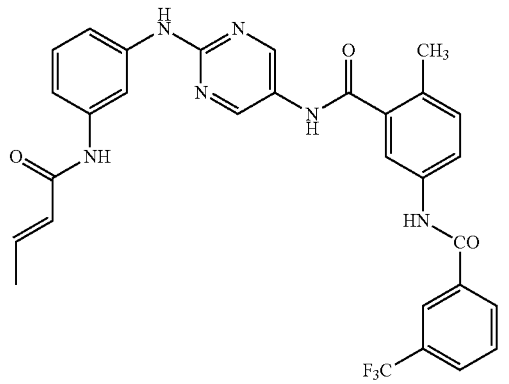 [SMILES: C/C=C/C(=O)Nc1cccc(Nc2ncc(NC(=O)c3cc(NC(=O)c4cccc(C(F)(F)F)c4)ccc3C)cn2)c1] | Similar to Compound 1, but in step 1 of Synthetic Scheme II, acryloyl chloride was replaced by 2-butenoyl chloride | HRMS (ESI) m/z calculated for C$_{30}$H$_{26}$F$_3$N$_6$O$_3$ (M + H)$^+$: 575.2018, found: 575.2015 | +++ |
| 3 | 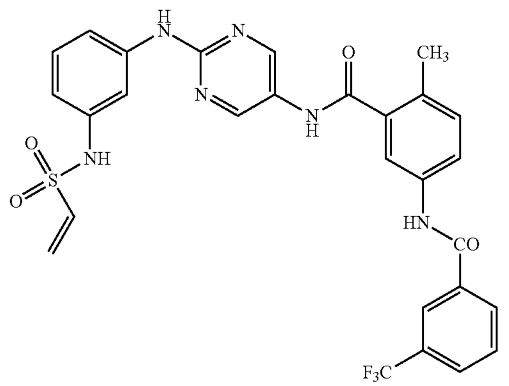 [SMILES: C=CS(=O)(=O)Nc1cccc(Nc2ncc(NC(=O)c3cc(NC(=O)c4cccc(C(F)(F)F)c4)ccc3C)cn2)c1] | Similar to Compound 1, but in step 1 of Synthetic Scheme II, acryloyl chloride was replaced by vinyl sulfonyl chloride | HRMS (ESI) m/z calculated for C$_{28}$H$_{24}$F$_3$N$_6$O$_4$S (M + H)$^+$: 597.1532, found: 597.1516 | +++ |
| 4 | 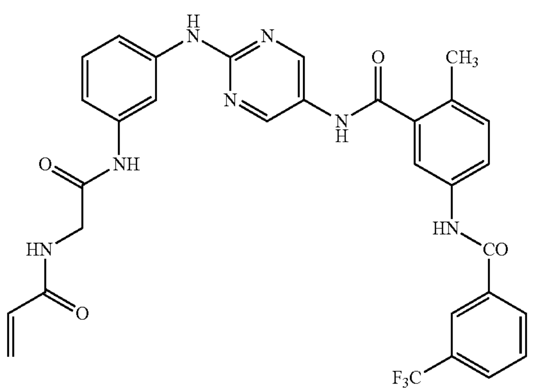 [SMILES: C=CC(=O)NCC(=O)Nc1cccc(Nc2ncc(NC(=O)c3cc(NC(=O)c4cccc(C(F)(F)F)c4)ccc3C)cn2)c1] | Synthesized according to Synthetic Scheme II | HRMS (ESI) m/z calculated for C$_{31}$H$_{27}$F$_3$N$_7$O$_4$ (M + H)$^+$: 618.2077, found: 618.2086 | +++ |
| 5 | 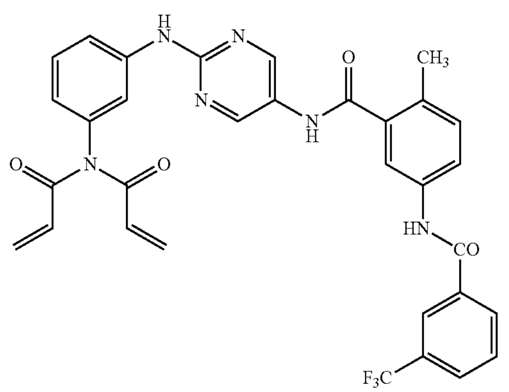 [SMILES: C=CC(=O)N(C(=O)C=C)c1cccc(Nc2ncc(NC(=O)c3cc(NC(=O)c4cccc(C(F)(F)F)c4)ccc3C)cn2)c1] | Synthesized according to Synthetic Scheme II, the difference lies in that excess amount of acryloyl chloride (>26 μL, 0.32 mmol) was used | HRMS (ESI) m/z calculated for C$_{32}$H$_{26}$F$_3$N$_6$O$_4$ (M + H)$^+$: 615.1968, found: 615.2026 | ++ |

TABLE 1-continued

Synthesis of the compounds of Examples and Btk IC$_{50}$ values

| Example | Structure | Synthetic Scheme | Structure Data | Efficacy |
|---|---|---|---|---|
| 6 | 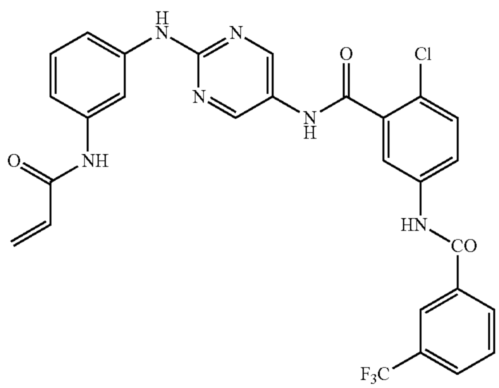 | Similar to Compound 1, but in step 4 of Synthetic Scheme I, 5-amino-2-methyl-benzoic acid was replaced by 5-amino-2-chlorobenzoic acid | HRMS (ESI) m/z calculated for C$_{28}$H$_{21}$ClF$_3$N$_6$O$_3$ (M + H)$^+$: 581.1316, found: 581.1326 | +++ |
| 7 | 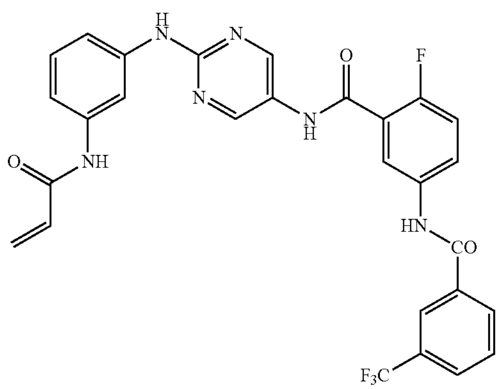 | Similar to Compound 1, but in step 4 of Synthetic Scheme I, 5-amino-2-methyl-benzoic acid was replaced by 5-amino-2-fluorobenzoic acid | $^1$H NMR(500 MHz, DMSO-d$_6$) δ 10.69 (s, 1H), 10.47 (s, 1H), 10.10 (s, 1H), 9.68 (s, 1H), 8.80 (s, 2H), 8.33 (s, 1H), 8.29 (d, J = 7.8 Hz, 1H), 8.13 (d, J = 6.0 Hz, 1H), 8.07 (s, 1H), 8.02-7.98 (m, 2H), 7.81 (t, J = 7.8 Hz, 1H), 7.44-7.38 (m, 3H), 7.21 (t, J = 8.1 Hz, 1H), 6.48 (dd, J = 10.2, 16.9 Hz, 1H), 6.26 (d, J = 17.0 Hz, 1H), 5.73 (d, J = 11.3 Hz, 1H). HRMS (ESI) m/z calculated for C$_{28}$H$_{21}$F$_4$N$_6$O$_3$ (M + H)+: 565.1611, found: 565.1624 | +++ |
| 8 | 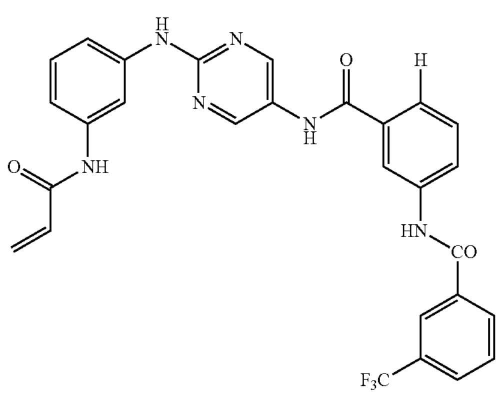 [SMILES: C=CC(=O)Nc1cccc(Nc2ncc(NC(=O)c3cc(NC(=O)c4cccc(C(F)(F)F)c4)ccc3F)cn2)c1] | Similar to Compound 1, but in step 4 of Synthetic Scheme I, 5-amino-2-methyl-benzoic acid was replaced by 3-amino-benzoic acid | $^1$H NMR(400 MHz, DMSO-d$_6$) δ 10.69 (s, 1H), 10.39 (s, 1H), 10.09 (s, 1H), 9.65 (s, 1H), 8.83 (s, 2H), 8.31 (d, J = 8.0 Hz, 1H), 8.07 (s, 1H), 8.04 (d, J = 1.3 Hz, 1H), 8.00 (d, J = 7.8 Hz, 1H), 7.79 (m, 2H), 7.57 (t, J = 7.9 Hz, 1H), 7.41-7.37 (m, 2H), 7.21 (t, J = 8.1 Hz, 1H), 6.48 (dd, J = 10.1, 16.9 Hz, 1H), 6.26 (dd, J = 2.1, 17.0 Hz, 1H), 5.73 (dd, J = 2.1, 10.2 Hz, 1H). HRMS (ESI) m/z calculated for C$_{28}$H$_{22}$F$_3$N$_6$O$_3$ (M + H)+: 547.1705, found: 547.1782 | +++ |

TABLE 1-continued

Synthesis of the compounds of Examples and Btk IC$_{50}$ values

| Example | Structure | Synthetic Scheme | Structure Data | Efficacy |
|---|---|---|---|---|
| 9 | 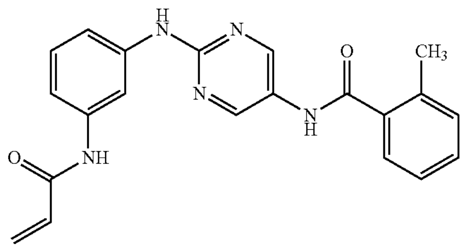 [SMILES: C=CC(=O)Nc1cccc(Nc2ncc(NC(=O)c3ccccc3C)cn2)c1] | Similar to Compound 1, but in step 5 of Synthestic Scheme I, Compound 5 was replaced by 2-methyl-benzoic acid | $^1$H NMR(400 MHz, CD$_3$OD) δ 8.75 (s, 1H), 8.13 (s, 1H), 7.50 (d, J = 7.6 Hz, 1H), 7.41-7.35 (m, 2H), 7.31-7.28 (m, 3H), 7.24 (t, J = 8.0 Hz, 1H), 6.45 (dd, J = 10.0, 16.9 Hz, 1H), 6.35 (dd, J = 1.6, 17.0 Hz, 1H), 5.76 (dd, J = 1.6, 10.1 Hz, 1H), 3.72 (t, J = 6.4 Hz, 2H), 2.47 (s, 3H), 1.88-1.85 (m, 2H). HRMS (ESI) m/z calculated for C$_{21}$H$_{20}$N$_5$O$_2$ (M + H)+: 374.1617, found: 374.1630 | +++ |
| 10 | 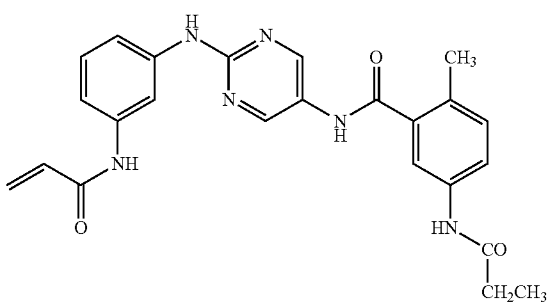 [SMILES: C=CC(=O)Nc1cccc(Nc2ncc(NC(=O)c3cc(NC(=O)CC)ccc3C)cn2)c1] | Similar to Compound 1, but in step 4 of Synthetic Scheme I, 3-(trifluoromethyl)benzoic acid was replaced by propionic acid | HRMS (ESI) m/z calculated for C$_{24}$H$_{24}$N$_6$NaO$_3$ (M + Na)$^+$: 467.1808, found: 467.1823 | ++ |
| 11 | 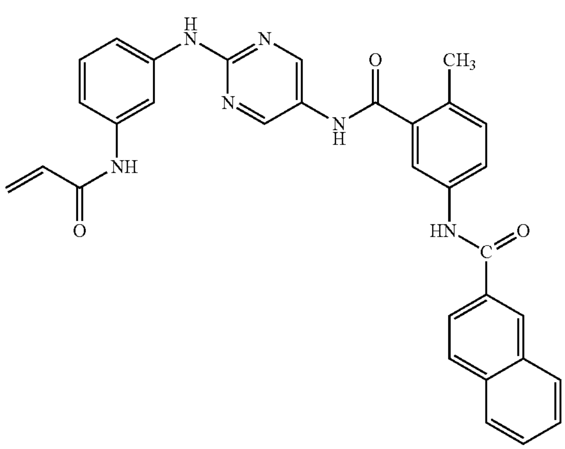 [SMILES: C=CC(=O)Nc1cccc(Nc2ncc(NC(=O)c3cc(NC(=O)c4ccc5ccccc5c4)ccc3C)cn2)c1] | Similar to Compound 1, but in step 4 of Synthetic Scheme I, 3-(trifluoromethyl)benzoic acid was replaced by 2-naphthoic acid | HRMS (ESI) m/z calculated for C$_{32}$H$_{27}$N$_6$O$_3$ (M + H)$^+$: 543.2145, found: 543.2126 | +++ |

TABLE 1-continued

Synthesis of the compounds of Examples and Btk IC$_{50}$ values

| Example | Structure | Synthetic Scheme | Structure Data | Efficacy |
|---|---|---|---|---|
| 12 | 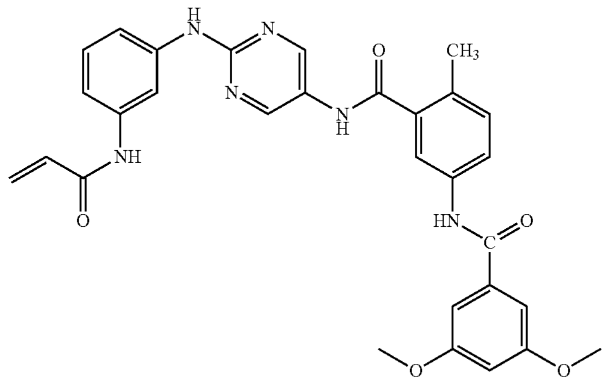 [SMILES: C=CC(=O)Nc1cccc(Nc2ncc(NC(=O)c3cc(NC(=O)c4cc(OC)cc(OC)c4)ccc3C)cn2)c1] | Similar to Compound 1, but in step 4 of Synthetic Scheme I, 3-(trifluoromethyl) benzoic acid was replaced by 3,5-dimethoxy-benzoic acid | HRMS (ESI) m/z calculated for C$_{30}$H$_{29}$N$_6$O$_5$ (M + H)$^+$: 553.2199, found: 553.2209 | +++ |
| 13 | 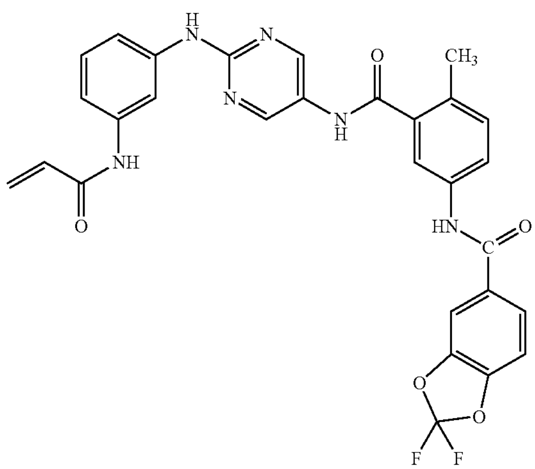 [SMILES: C=CC(=O)Nc1cccc(Nc2ncc(NC(=O)c3cc(NC(=O)c4ccc5c(c4)OC(F)(F)O5)ccc3C)cn2)c1] | Similar to Compound 1, but in Step 4 of Synthetic Scheme I, 3-(trifluoromethyl) benzoic acid was replaced by 2,2-difluorobenzo[d][1,3]dioxole-5-carboxylic acid | HRMS (ESI) m/z calculated for C$_{29}$H$_{23}$F$_2$N$_6$O$_5$ (M + H)$^+$: 573.1698, found: 573.1712 | +++ |
| 14 | 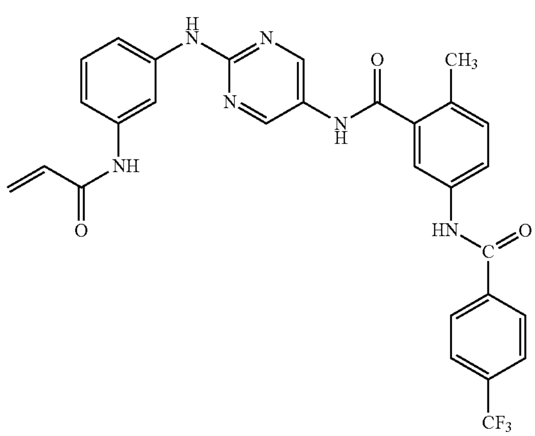 [SMILES: C=CC(=O)Nc1cccc(Nc2ncc(NC(=O)c3cc(NC(=O)c4ccc(C(F)(F)F)cc4)ccc3C)cn2)c1] | Similar to Compound 1, but in step 4 of Synthetic Scheme I, 3-(trifluoromethyl) benzoic acid was replaced by 4-(trifluoromethyl) benzoic acid | HRMS (ESI) m/z calculated for C$_{29}$H$_{23}$F$_3$N$_6$NaO$_3$ (M + Na)$^+$: 583.1681, found: 583.1711 | +++ |

TABLE 1-continued

Synthesis of the compounds of Examples and Btk IC₅₀ values

| Example | Structure | Synthetic Scheme | Structure Data | Efficacy |
|---|---|---|---|---|
| 15 | 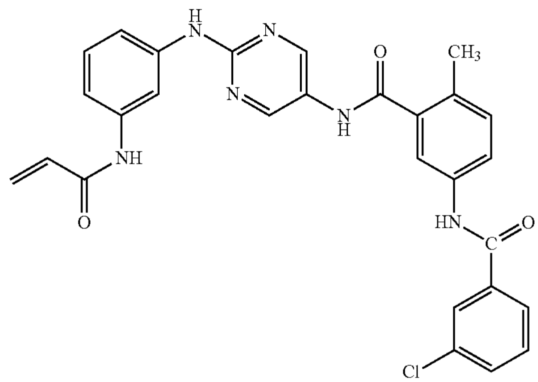 [SMILES: C=CC(=O)Nc1cccc(Nc2ncc(NC(=O)c3cc(NC(=O)c4cccc(Cl)c4)ccc3C)cn2)c1] | Similar to Compound 1, but in step 4 of Synthetic Scheme I, 3-(trifluoromethyl)benzoic acid was replaced by 3-chlorobenzoic acid | HRMS (ESI) m/z calculated for $C_{28}H_{24}ClN_6O_3$ $(M + H)^+$: 527.1598, found: 527.1576 | +++ |
| 16 | 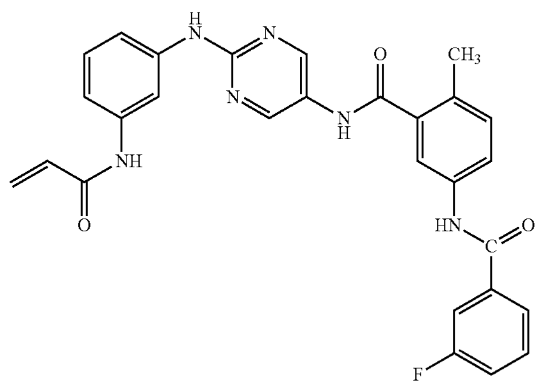 [SMILES: C=CC(=O)Nc1cccc(Nc2ncc(NC(=O)c3cc(NC(=O)c4cccc(F)c4)ccc3C)cn2)c1] | Similar to Compound 1, but in step 4 of Synthetic Scheme I, 3-(trifluoromethyl)benzoic acid was replaced by 3-fluorobenzoic acid | HRMS (ESI) m/z calculated for $C_{28}H_{23}FN_6NaO_3$ $(M + Na)^+$: 533.1713, found: 533.1709 | +++ |
| 17 | 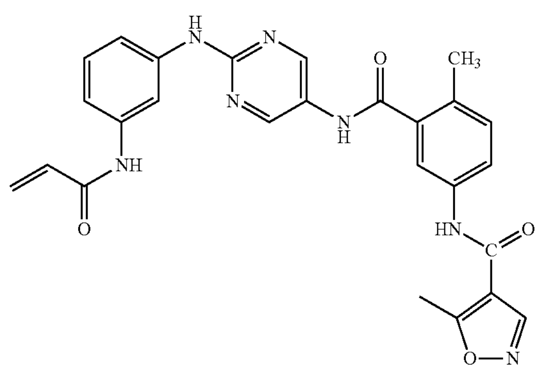 [SMILES: C=CC(=O)Nc1cccc(Nc2ncc(NC(=O)c3cc(NC(=O)c4cnoc4C)ccc3C)cn2)c1] | Similar to Compound 1, but in step 4 of Synthetic Scheme I, 3-(trifluoromethyl)benzoic acid was replaced by 5-methylisoxazole-4-carboxylic acid | HRMS (ESI) m/z calculated for $C_{26}H_{24}N_7O_4$ $(M + H)^+$: 498.1890, found: 498.1891 | ++ |
| 18 | 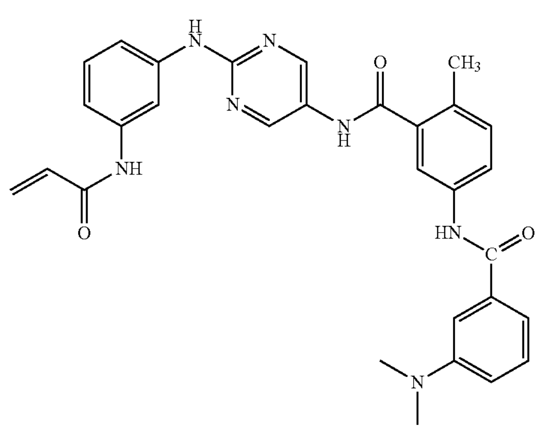 [SMILES: C=CC(=O)Nc1cccc(Nc2ncc(NC(=O)c3cc(NC(=O)c4cccc(N(C)C)c4)ccc3C)cn2)c1] | Similar to Compound 1, but in step 4 of Synthetic Scheme I, 3-(trifluoromethyl)benzoic acid was replaced by 3-(dimethylamino)benzoic acid | HRMS (ESI) m/z calculated for $C_{30}H_{29}N_7NaO_3$ $(M + Na)^+$: 558.2230, found: 558.2242 | +++ |

TABLE 1-continued

Synthesis of the compounds of Examples and Btk IC$_{50}$ values

| Example | Structure | Synthetic Scheme | Structure Data | Efficacy |
|---|---|---|---|---|
| 19 | 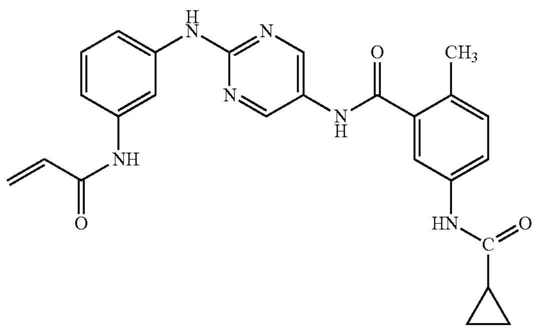 [SMILES: C=CC(=O)Nc1cccc(Nc2ncc(NC(=O)c3cc(NC(=O)C4CC4)ccc3C)cn2)c1] | Similar to Compound 1, but in step 4 of Synthetic Scheme I, 3-(trifluoromethyl)benzoic acid was replaced by cyclopropanecarboxylic acid | HRMS (ESI) m/z calculated for C$_{25}$H$_{24}$N$_6$NaO$_3$ (M + Na)$^+$: 479.1808, found: 479.1820 | ++ |
| 20 | 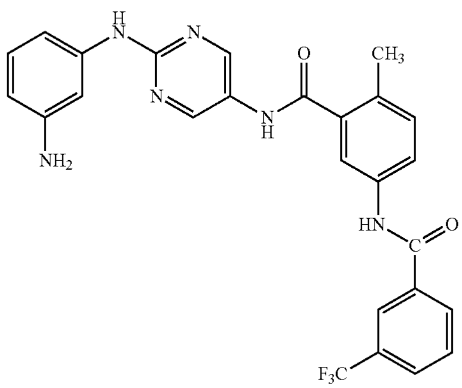 [SMILES: Cc1ccc(NC(=O)c2cccc(C(F)(F)F)c2)cc1C(=O)Nc1cnc(Nc2cccc(N)c2)nc1] | Synthesized according to Synthetic Scheme I | HRMS (ESI) m/z calculated for C$_{26}$H$_{22}$F$_3$N$_6$O$_2$ (M + H)$^+$: 507.1756, found: 507.1737 | +++ |
| 21 | 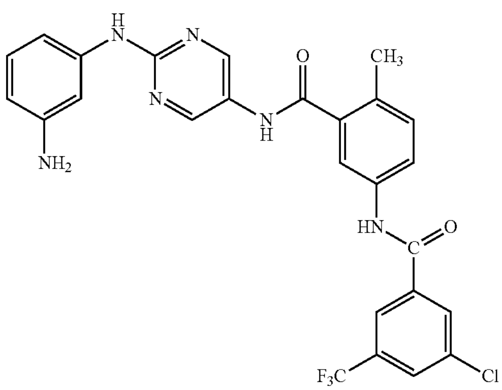 [SMILES: Cc1ccc(NC(=O)c2cc(Cl)cc(C(F)(F)F)c2)cc1C(=O)Nc1cnc(Nc2cccc(N)c2)nc1] | Similar to Compound 20, but in step 4 of Synthetic Scheme I, 3-(trifluoromethyl)benzoic acid was replaced by 3-chloro-5-(trifluoromethyl)benzoic acid | HRMS (ESI) m/z calculated for C$_{26}$H$_{21}$ClF$_3$N$_6$O$_2$ (M + H)$^+$: 541.1367, found: 541.1344 | +++ |
| 22 | 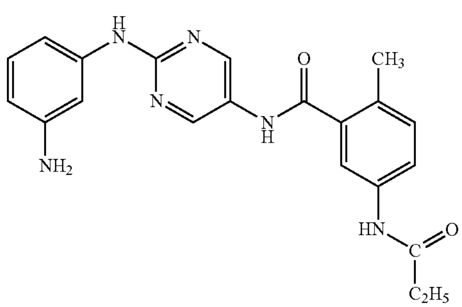 [SMILES: CCC(=O)Nc1ccc(C)c(C(=O)Nc2cnc(Nc3cccc(N)c3)nc2)c1] | Similar to Compound 20, but in step 4 of Synthetic Scheme I, 3-(trifluoromethyl)benzoic acid was replaced by propionic acid | $^1$H NMR(500 MHz, DMSO-d$_6$) δ 10.30 (s, 1H), 9.55 (s, 1H), 9.30 (s, 1H), 8.74 (s, 2H), 7.75 (s, 1H), 7.58 (d, J = 8.2 Hz, 1H), 7.22 (d, J = 8.3 Hz, 1H), 7.09 (s, 1H), 6.89 (td, J = 7.8, 18.0 Hz, 2H), 6.19 (d, J = 7.6 Hz, 1H), 5.13 (brs, 2H), 2.33 (s, 5H), 1.08 (t, J = 7.8, 6.2 Hz, 3H). HRMS (ESI) m/z calculated for C$_{21}$H$_{23}$N$_6$O$_2$ (M + H)+: 391.1882, found: 391.1913 | + |

TABLE 1-continued

Synthesis of the compounds of Examples and Btk IC$_{50}$ values

| Example | Structure | Synthetic Scheme | Structure Data | Efficacy |
|---|---|---|---|---|
| 23 | 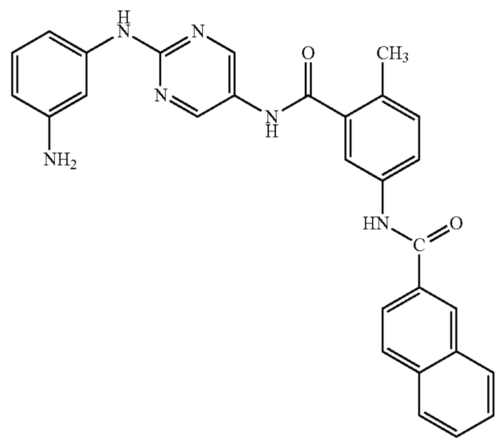 [SMILES: Cc1ccc(NC(=O)c2ccc3ccccc3c2)cc1C(=O)Nc1cnc(Nc2cccc(N)c2)nc1] | Similar to Compound 20, but in step 4 of Synthetic Scheme I, 3-(trifluoromethyl) benzoic acid was replaced by 2-naphthoic acid | $^1$H NMR(400 MHz, DMSO-d$_6$) δ 10.56 (s, 1H), 10.40 (s, 1H), 9.34 (s, 1H), 8.79 (s, 2H), 8.62 (s, 1H), 8.11-8.02 (m, 5H), 7.89 (d, J = 8.3 Hz, 1H), 7.66 (s, 2H), 7.34 (d, J = 10.5 Hz, 1H), 7.11 (s, 1H), 6.94-6.86 (m, 2H), 6.20 (d, J = 7.4 Hz, 1H), 5.16 (brs, 2H), 2.40 (s, 3H). HRMS (ESI) m/z calculated for C$_{29}$H$_{25}$N$_6$O$_2$ (M + H)+: 489.2039, found: 489.2048 | +++ |
| 24 | 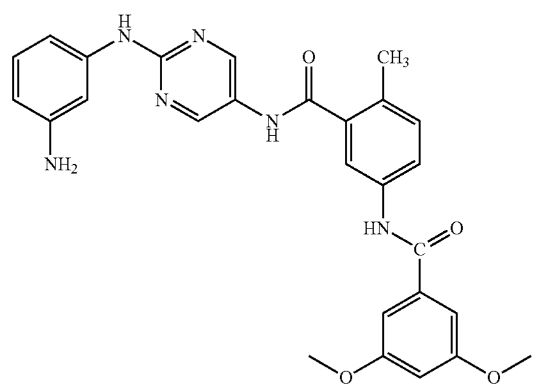 [SMILES: COc1cc(OC)cc(C(=O)Nc2ccc(C)c(C(=O)Nc3cnc(Nc4cccc(N)c4)nc3)c2)c1] | Similar to Compound 20, but in step 4 of Synthetic Scheme I, 3-(trifluoromethyl) benzoic acid was replaced by 3,5-dimethoxy-benzoic acid | HRMS (ESI) m/z calculated for C$_{27}$H$_{27}$N$_6$O$_4$ (M + H)$^+$: 499.2094, found: 499.2096 | +++ |
| 25 | 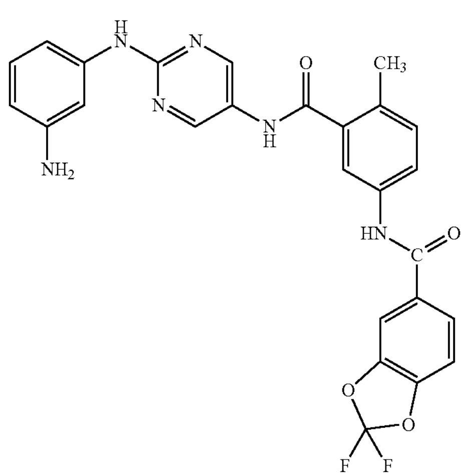 [SMILES: Cc1ccc(NC(=O)c2ccc3c(c2)OC(F)(F)O3)cc1C(=O)Nc1cnc(Nc2cccc(N)c2)nc1] | Similar to Compound 20, but in step 4 of Synthetic Scheme I, 3-(trifluoromethyl) benzoic acid was replaced by 2,2-difluoro-benzo[d][1,3]dioxole-5-carboxylic acid | HRMS (ESI) m/z calculated for C$_{26}$H$_{21}$F$_2$N$_6$O$_4$ (M + H)$^+$: 519.1592, found: 519.1580 | +++ |

TABLE 1-continued

Synthesis of the compounds of Examples and Btk IC$_{50}$ values

| Example | Structure | Synthetic Scheme | Structure Data | Efficacy |
|---|---|---|---|---|
| 26 | 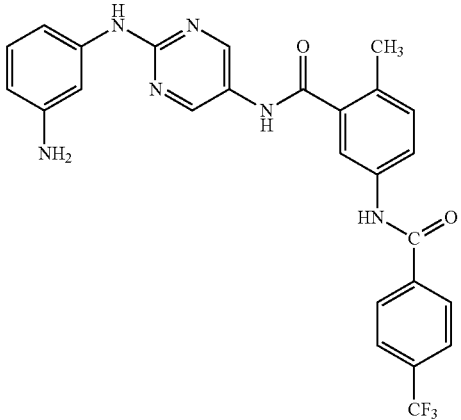 [SMILES: Cc1ccc(NC(=O)c2ccc(C(F)(F)F)cc2)cc1C(=O)Nc1cnc(Nc2cccc(N)c2)nc1] | Similar to Compound 20, but in step 4 of Synthetic Scheme I, 3-(trifluoromethyl) benzoic acid was replaced by 4-(trifluoromethyl) benzoic acid | HRMS (ESI) m/z calculated for $C_{26}H_{22}F_3N_6O_2$ (M + H)$^+$: 507.1756, found: 507.1754 | +++ |
| 27 | 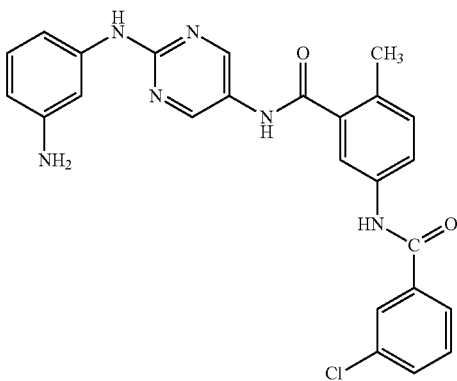 [SMILES: Cc1ccc(NC(=O)c2cccc(Cl)c2)cc1C(=O)Nc1cnc(Nc2cccc(N)c2)nc1] | Similar to Compound 20, but in step 4 of Synthetic Scheme I, 3-(trifluoromethyl) benzoic acid was replaced by 3-chlorobenzoic acid | $^1$H NMR(500 MHz, DMSO-d$_6$) δ 10.43 (s, 1H), 10.34 (s, 1H), 9.27 (s, 1H), 8.77 (s, 2H), 8.04 (s, 1H), 7.94 (s, 2H), 7.82 (d, J = 8.2 Hz, 1H), 7.67 (d, J = 8.0 Hz, 1H), 7.58 (t, J = 7.8 Hz, 1H), 7.31 (d, J = 8.4 Hz, 1H), 7.08 (s, 1H), 6.92-6.85 (m, 2H), 6.19 (d, J = 7.6 Hz, 1H), 4.92 (s, 2H), 2.39 (s, 3H). HRMS (ESI) m/z calculated for $C_{25}H_{22}ClN_6O_2$ (M + H)+: 473.1493, found: 473.1519 | +++ |
| 28 | 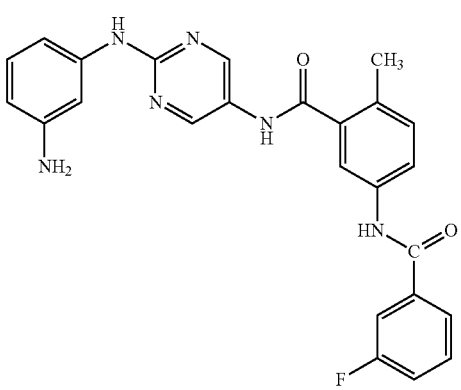 [SMILES: Cc1ccc(NC(=O)c2cccc(F)c2)cc1C(=O)Nc1cnc(Nc2cccc(N)c2)nc1] | Similar to Compound 20, but in step 4 of Synthetic Scheme I, 3-(trifluoromethyl) benzoic acid was replaced by 3-fluorobenzoic acid | $^1$H NMR(400 MHz, DMSO-d$_6$) δ 10.44 (s, 1H), 10.38 (s, 1H), 9.32 (s, 1H), 8.77 (s, 2H), 7.95 (d, J = 2.1 Hz, 1H), 7.85-7.78 (m, 3H), 7.64-7.58 (m, 1H), 7.49-7.44 (m, 1H), 7.32 (d, J = 8.4 Hz, 1H), 7.08 (s, 1H), 6.92-6.84 (m, 2H), 6.18 (d, J = 7.6 Hz, 1H), 4.96 (s, 2H), 2.39 (s, 3H). HRMS (ESI) m/z calculated for $C_{25}H_{22}FN_6O_2$ (M + H)+: 457.1788, found: 457.1844 | ++ |

TABLE 1-continued

Synthesis of the compounds of Examples and Btk IC$_{50}$ values

| Example | Structure | Synthetic Scheme | Structure Data | Efficacy |
|---|---|---|---|---|
| 29 | 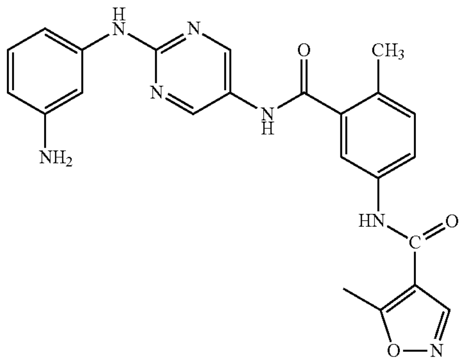 [SMILES: Cc1ccc(NC(=O)c2cnoc2C)cc1C(=O)Nc1cnc(Nc2cccc(N)c2)nc1] | Similar to Compound 20, but in step 4 of Synthetic Scheme I, 3-(trifluoromethyl) benzoic acid was replaced by 5-methylisoxazole-4-carboxylic acid | $^1$H NMR(400 MHz, DMSO-d$_6$) δ 10.36 (s, 1H), 10.15 (s, 1H), 9.32 (s, 1H), 9.09 (s, 1H), 8.76 (s, 2H), 7.85 (d, J = 1.9 Hz, 1H), 7.73 (dd, J = 2.0, 8.2 Hz, 1H), 7.31 (d, J = 8.4 Hz, 1H), 7.08 (s, 1H), 6.92-6.84 (m, 2H), 6.18 (d, J = 7.6 Hz, 1H), 4.96 (s, 2H), 2.70 (s, 3H), 2.38 (s, 3H). HRMS (ESI) m/z calculated for C$_{25}$H$_{22}$N$_7$O$_3$ (M + H)+: 444.1784, found: 444.1823 | ++ |
| 30 | 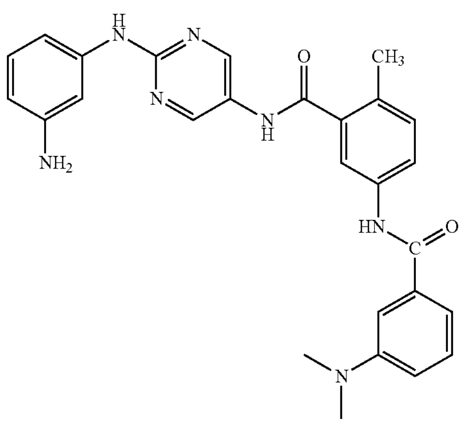 [SMILES: Cc1ccc(NC(=O)c2cccc(N(C)C)c2)cc1C(=O)Nc1cnc(Nc2cccc(N)c2)nc1] | Similar to Compound 20, but in step 4 of Synthetic Scheme I, 3-(trifluoromethyl) benzoic acid was replaced by 3-(dimethylamino) benzoic acid | $^1$H NMR(400 MHz, DMSO-d$_6$) δ 10.53 (s, 1H), 10.38 (s, 1H), 9.33 (s, 1H), 8.80 (s, 2H), 8.00 (s, 1H), 7.86 (d, J = 8.3 Hz, 1H), 7.34-7.27 (m, 4H), 7.09 (s, 1H), 6.94-6.84 (m, 3H), 6.18 (d, J = 7.5 Hz, 1H), 4.97 (s, 2H), 2.98 (s, 6H), 2.39 (s, 3H). HRMS (ESI) m/z calculated for C$_{27}$H$_{28}$N$_7$O$_2$ (M + H)+: 482.2304, found: 482.2508 | +++ |
| 31 | 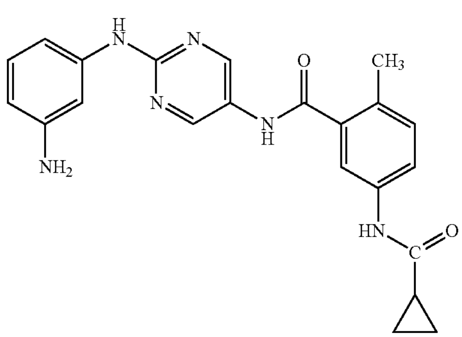 [SMILES: Cc1ccc(NC(=O)C2CC2)cc1C(=O)Nc1cnc(Nc2cccc(N)c2)nc1] | Similar to Compound 20, but in step 4 of Synthetic Scheme I, 3-(trifluoromethyl) benzoic acid was replaced by cyclopropanecarboxylic acid | $^1$H NMR(400 MHz, DMSO-d$_6$) δ 10.30 (d, J = 5.4 Hz, 2H), 9.32 (s, 1H), 8.75 (s, 2H), 7.78 (s, 1H), 7.58 (d, J = 8.2 Hz, 1H), 7.22 (d, J = 8.4 Hz, 1H), 7.07 (s, 1H), 6.91-6.83 (m, 2H), 6.17 (d, J = 7.6 Hz, 1H), 4.96 (s, 2H), 2.33 (s, 3H), 1.78 (t, J = 5.8 Hz, 1H), 0.80 (t, J = 4.2 Hz, 4H). HRMS (ESI) m/z calculated for C$_{22}$H$_{23}$N$_6$O$_2$ (M + H)+: 403.1882, found: 403.2030 | + |

TABLE 1-continued

Synthesis of the compounds of Examples and Btk IC$_{50}$ values

| Example | Structure | Synthetic Scheme | Structure Data | Efficacy |
|---|---|---|---|---|
| 32 | 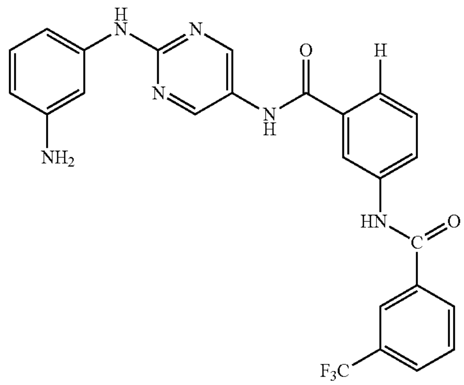 | Similar to Compound 20, but in step 4 of Synthetic Scheme I, 5-amino-2-methyl-benzoic acid was replaced by 3-amino-benzoic acid | $^1$H NMR(400 MHz, DMSO-d$_6$) δ 10.70 (s, 1H), 10.36 (s, 1H), 9.32 (s, 1H), 8.78 (s, 2H), 8.36-8.31 (m, 3H), 8.06 (d, J = 8.2 Hz, 1H), 7.99 (d, J = 7.8 Hz, 1H), 7.84-7.76 (m, 2H), 7.57 (t, J = 7.9 Hz, 1H), 7.09 (s, 1H), 6.93-6.85 (m, 2H), 6.19 (d, J = 7.5 Hz, 1H), 4.98 (s, 2H). HRMS (ESI) m/z calculated for C$_{25}$H$_{20}$F$_3$N$_6$O$_2$ (M + H)+: 493.1600, found: 493.1648 | ++ |
| 33 | 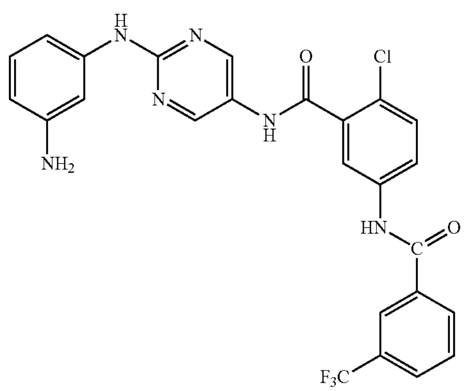 [SMILES: Nc1cccc(Nc2ncc(NC(=O)c3cc(NC(=O)c4cccc(C(F)(F)F)c4)ccc3Cl)cn2)c1] | Similar to Compound 20, but in step 4 of Synthetic Scheme I, 5-amino-2-methyl-benzoic acid was replaced by 5-amino-2-chlorobenzoic acid | HRMS (ESI) m/z calculated for C$_{25}$H$_{19}$ClF$_3$N$_6$O$_2$ (M + H)$^+$: 527.1210, found: 527.1193 | +++ |
| 34 | 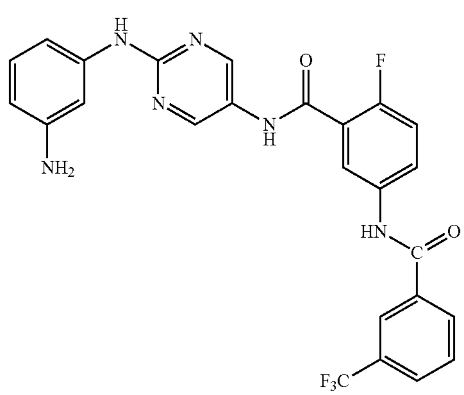 | Similar to Compound 20, but in step 4 of Synthetic Scheme I, 5-amino-2-methyl-benzoic acid was replaced by 5-amino-2-fluorobenzoic acid | $^1$H NMR(500 MHz, CD$_3$OD) δ 8.70 (s, 2H), 8.27 (s, 1H), 8.20 (d, J = 7.9 Hz, 1H), 8.13 (dd, J = 2.7, 6.3 Hz, 1H), 7.94-7.88 (m, 2H), 7.72 (t, J = 7.8 Hz, 1H), 7.27 (t, J = 9.5 Hz, 1H), 7.20 (t, J = 2.1 Hz, 1H), 7.02 (t, J = 8.0 Hz, 1H), 6.92 (dd, J = 1.0, 8.0 Hz, 1H), 6.40 (dd, J = 1.3, 7.8 Hz, 1H), 4.56 (s, 1H). HRMS (ESI) m/z calculated for C$_{25}$H$_{19}$F$_4$N$_6$O$_2$ (M + H)$^+$: 511.1506, found: 511.1548 | +++ |

TABLE 1-continued

Synthesis of the compounds of Examples and Btk $IC_{50}$ values

| Example | Structure | Synthetic Scheme | Structure Data | Efficacy |
|---|---|---|---|---|
| 35 | 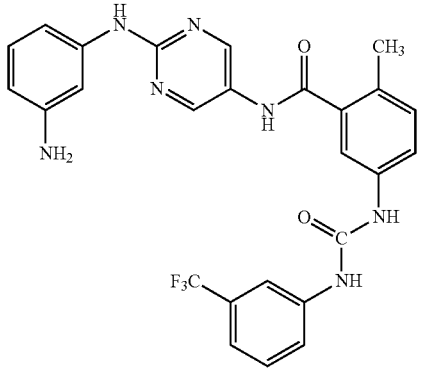 [SMILES: Cc1ccc(NC(=O)Nc2cccc(C(F)(F)F)c2)cc1C(=O)Nc1cnc(Nc2cccc(N)c2)nc1] | Similar to Compound 20, but in step 4 of Synthetic Scheme I, 3-(trifluoromethyl) benzoic acid was replaced by 3-(trifluoromethyl) phenyl carbamic acid | HRMS (ESI) m/z calculated for $C_{26}H_{23}F_3N_7O_2$ $(M + H)^+$: 522.1865, found: 522.1852 | +++ |
| 36 | 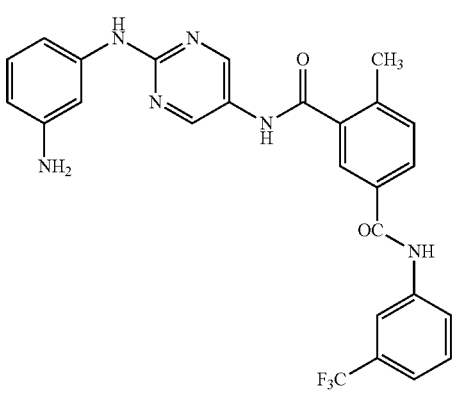 | Similar to Compound 20, but in step 5 of Synthetic Scheme I, Compound 5 was replaced by 2-methyl-5-(3-(trifluoromethyl) phenyl carbamoyl) benzoic acid | HRMS (ESI) m/z calculated for $C_{25}H_{20}F_3N_6O_2$ $(M + H)^+$: 493.1600, found: 493.1601 | ++ |
| 37 | 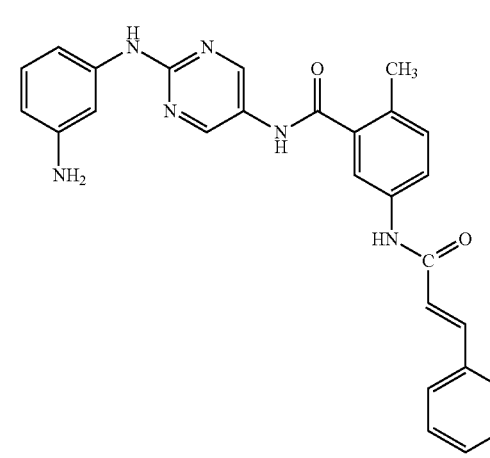 | Similar to Compound 20, but in step 4 of Synthetic Scheme I, 3-(trifluoromethyl) benzoic acid was replaced by cinnamic acid (phenyl-2-acrylic acid) | HRMS (ESI) m/z calculated for $C_{27}H_{25}N_6O_2$ $(M + H)^+$: 465.2039, found: 465.2037 | ++ |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula (I)

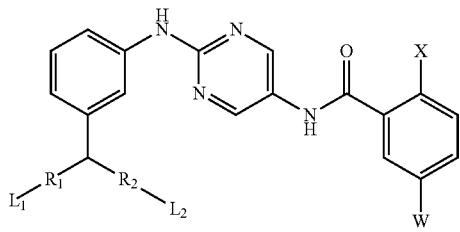

or a pharmaceutically acceptable salt thereof, wherein:
W is selected from H, $C_{1-6}$ alkyl, —(NH—CO)$_n$-L-L$_3$, —(CO—NH)$_n$-L-L$_3$, and —(NH—CO)$_n$—NH-L-L$_3$;
wherein:
L is a bond, $C_{1-3}$ alkylene or $C_{2-3}$ alkenylene;
L$_3$ is $C_{3-8}$ cycloalkyl, aryl or heteroaryl, each optionally substituted with 1, 2 or 3 substituents selected from the group consisting of halogen, amino, $C_{1-6}$ alkyl, $C_{1-6}$ alkoxyl, halo-$C_{1-6}$ alkyl;
n is an integer of 0 or 1;
X is selected from H, halogen, and $C_{1-6}$ alkyl;
R$_1$ and R$_2$, same or different from each other, are each independently selected from H, C(O) and S(O)$_2$;
L$_1$ and L$_2$, same or different from each other, are each independently selected from $C_{2-3}$ alkenyl optionally substituted with $C_{1-3}$ alkyl, and $C_{1-3}$ alkyl-NHC(O)—$C_{2-3}$ alkenyl;
with the provisos that when R$_1$ is H, L$_1$ is not present; and when R$_2$ is H, L$_2$ is not present.

2. The compound of claim 1, or a pharmaceutically acceptable salt thereof, wherein W is selected from H, ethyl, —(NH—CO)$_n$-L-L$_3$, —(CO—NH)$_n$-L-L$_3$, and —(NH—CO)$_n$—NH-L-L$_3$,
wherein:
L is a bond or vinylene;
L$_3$ is cyclopropyl, phenyl, naphthyl, isoxazolyl or benzo-[d][1,3]-dioxole group optionally substituted with 1 or 2 substituents selected from F, Cl, amino, methoxyl and CF$_3$;
n is an integer of 1.

3. The compound of claim 1, or a pharmaceutically acceptable salt thereof, wherein X is selected from H, F, Cl, and methyl.

4. The compound of claim 1, or a pharmaceutically acceptable salt thereof, wherein
R$_1$ and R$_2$, same or different from each other, are each independently selected from H, C(O) and S(O)$_2$;
L$_1$ and L$_2$, same or different from each other, are each independently selected form $C_{2-3}$ alkenyl, and methyl-NHC(O)-ethenyl;
with the provisos that when R$_1$ is H, L$_1$ is not present; and when R$_2$ is H, L$_2$ is not present.

5. The compound of claim 1, or a pharmaceutically acceptable salt thereof, wherein
W is selected from H, ethyl, —(NH—CO)$_n$-L-L$_3$, —(CO—NH)$_n$-L-L$_3$, and —(NH—CO)$_n$—NH-L-L$_3$;
wherein:
L is a bond or vinylene;
L$_3$ is cyclopropyl, phenyl, naphthyl, isoxazolyl or benzo-[d][1,3]-dioxole group optionally substituted with 1 or 2 substituents selected from F, Cl, amino, methoxyl and CF$_3$;
n is an integer of 1;
X is selected from H, F, Cl, and methyl;
R$_1$ and R$_2$, same or different from each other, are each independently selected from H, C(O) and S(O)$_2$;
L$_1$ and L$_2$, same or different from each other, are each independently selected form $C_{2-3}$ alkenyl, and methyl-NHC(O)-ethenyl;
with the provisos that when R$_1$ is H, L$_1$ is not present; and when R$_2$ is H, L$_2$ is not present.

6. A compound selected from:

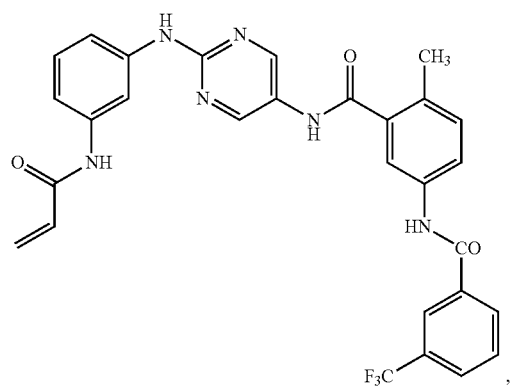

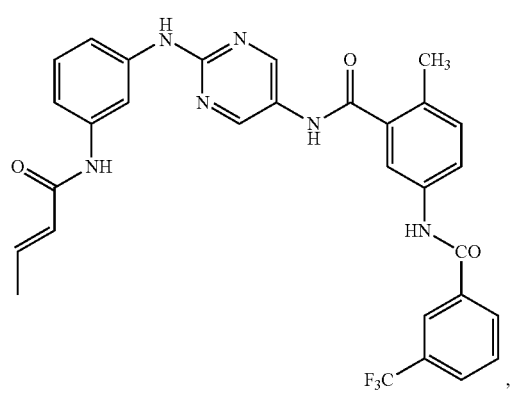

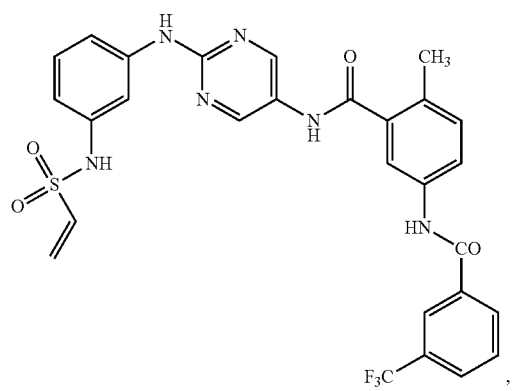

-continued

57
-continued
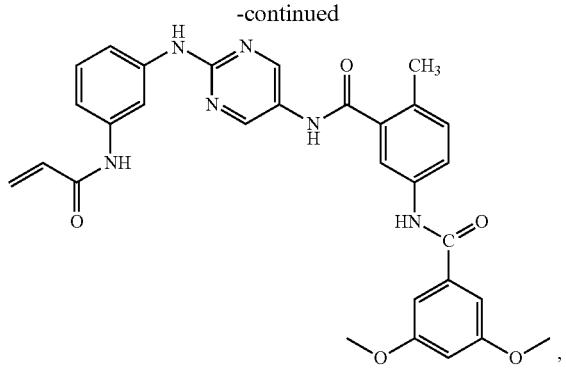
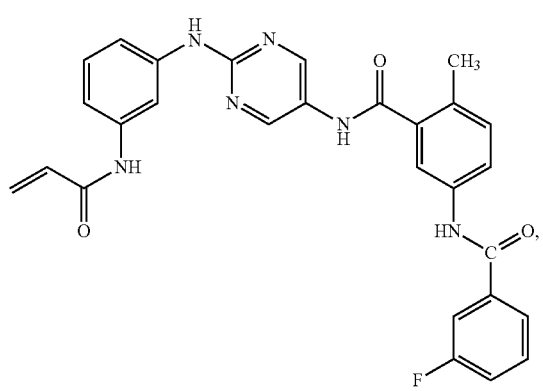
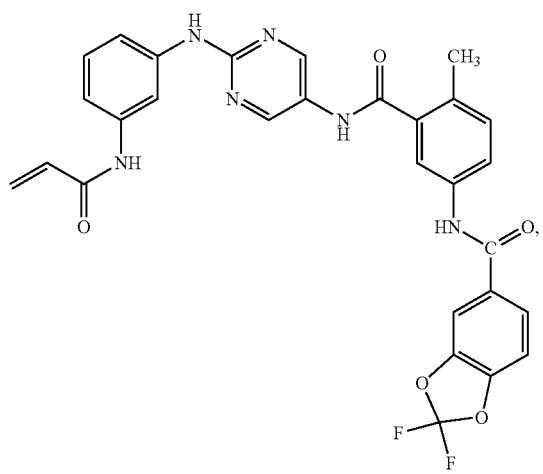
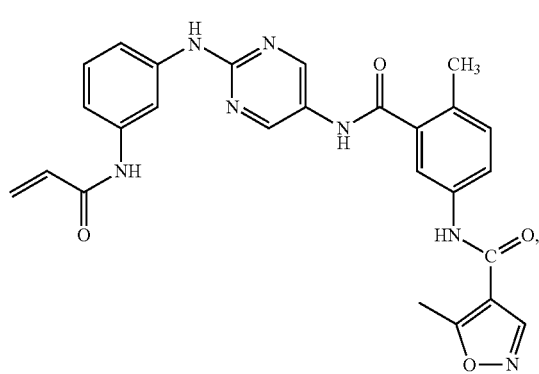
58
-continued
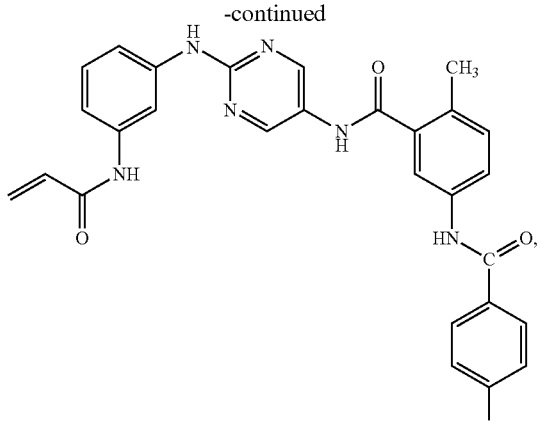
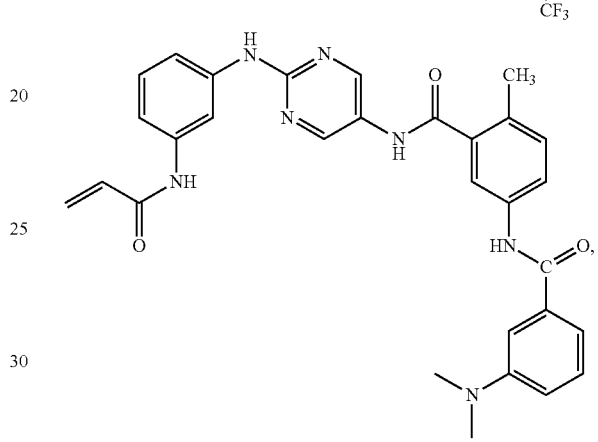
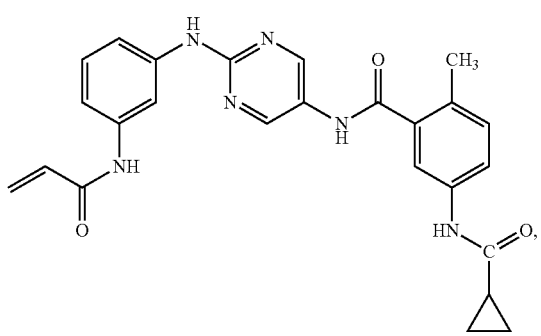
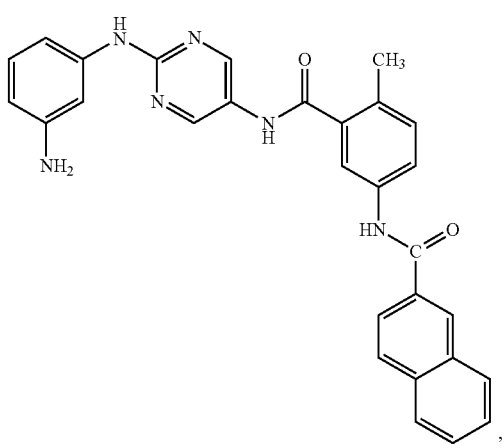

59
-continued
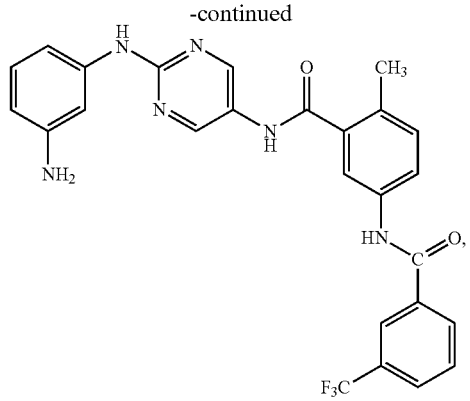
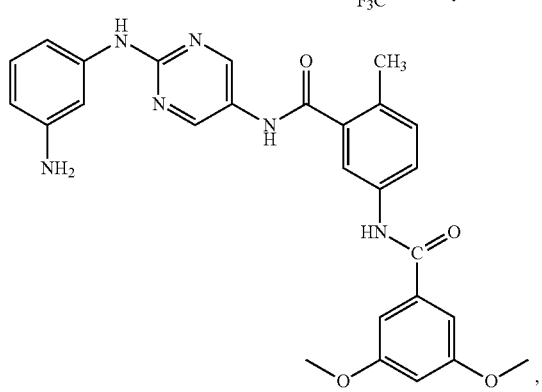
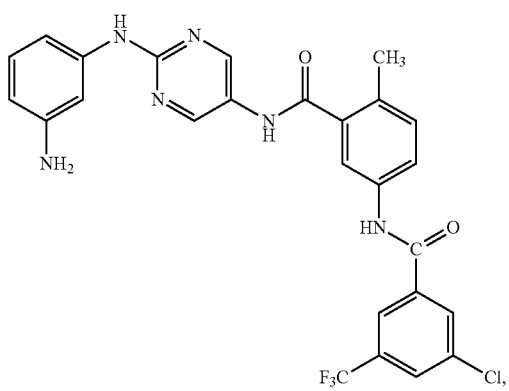
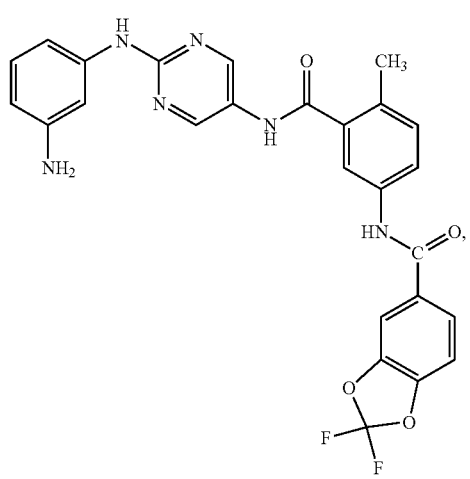
60
-continued
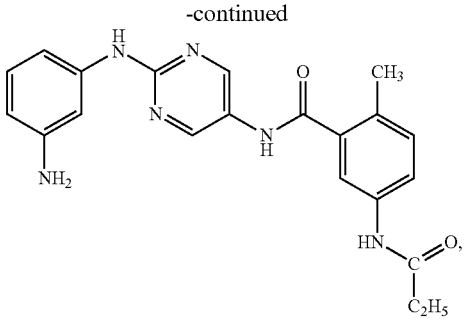
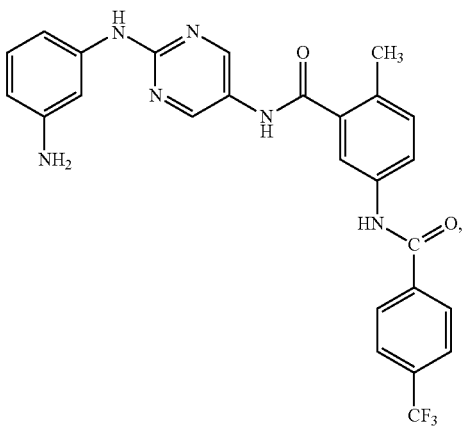
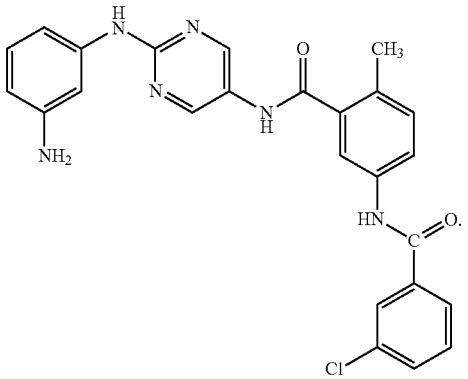
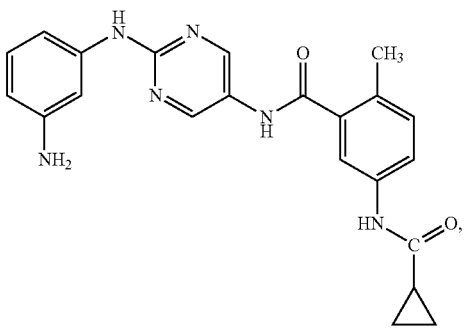

-continued
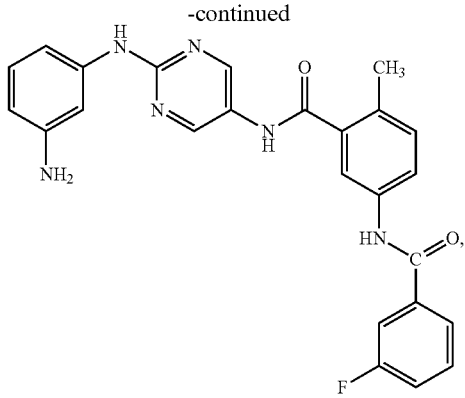
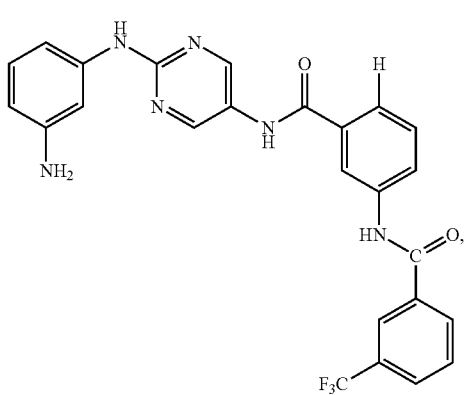
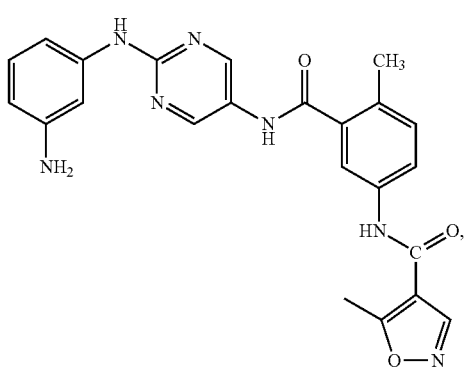
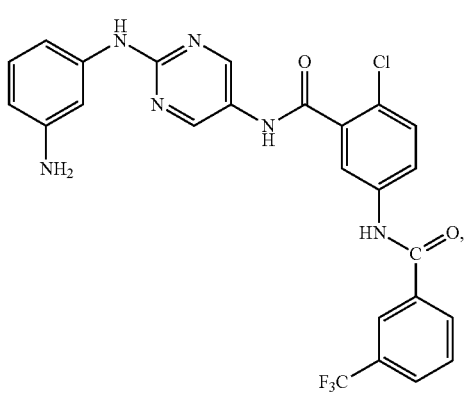
-continued
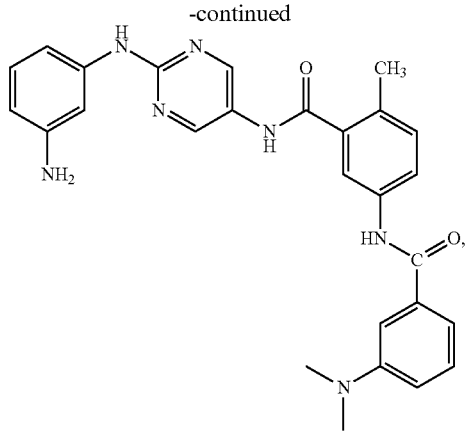
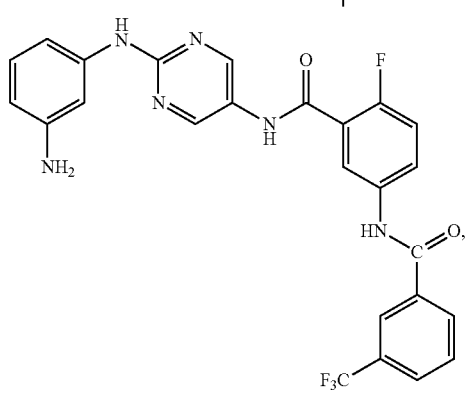
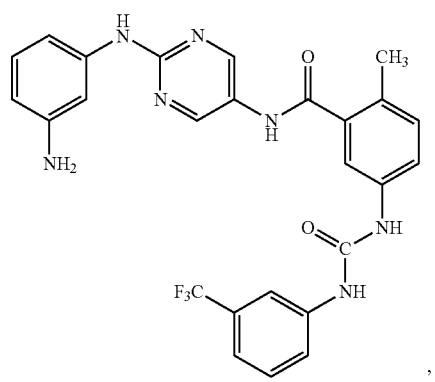
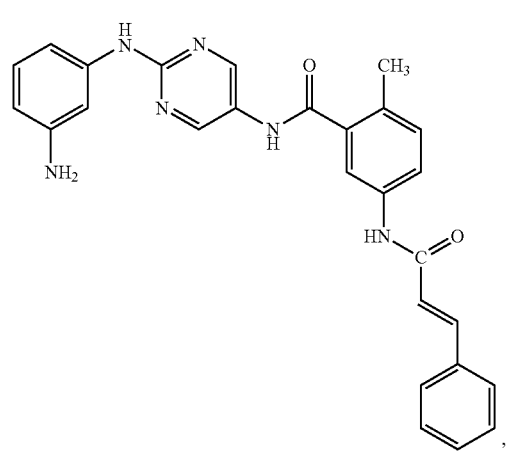

-continued

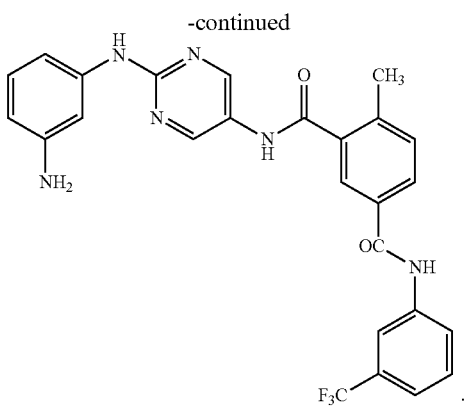

7. The pharmaceutical composition comprising a therapeutically effective amount of the compound of claim 1 and a pharmaceutically acceptable excipient.

8. The pharmaceutical composition comprising a therapeutically effective amount of the compound of claim 2 and a pharmaceutically acceptable excipient.

9. The pharmaceutical composition comprising a therapeutically effective amount of the compound of claim 3 and a pharmaceutically acceptable excipient.

10. The pharmaceutical composition comprising a therapeutically effective amount of the compound of claim 4 and a pharmaceutically acceptable excipient.

11. The pharmaceutical composition comprising a therapeutically effective amount of the compound of claim 5 and a pharmaceutically acceptable excipient.

12. The pharmaceutical composition comprising a therapeutically effective amount of the compound of claim 6 and a pharmaceutically acceptable excipient.

13. The method for treating rheumatoid arthritis, comprising administering to a subject in need thereof the compound of claim 1.

14. The method for treating rheumatoid arthritis, comprising administering to a subject in need thereof the compound of claim 2.

15. The method for treating rheumatoid arthritis, comprising administering to a subject in need thereof the compound of claim 3.

16. The method for treating rheumatoid arthritis, comprising administering to a subject in need thereof the compound of claim 4.

17. The method for treating rheumatoid arthritis, comprising administering to a subject in need thereof the compound of claim 5.

18. The method for treating rheumatoid arthritis, comprising administering to a subject in need thereof the compound of claim 6.

19. A method for treating rheumatoid arthritis, comprising administering to a subject in need thereof the pharmaceutical composition of claim 7.

20. The method of claim 13, wherein the subject is a human.

21. The method of claim 14, wherein the subject is a human.

22. The method of claim 15, wherein the subject is a human.

23. The method of claim 16, wherein the subject is a human.

24. The method of claim 17, wherein the subject is a human.

25. The method of claim 18, wherein the subject is a human.

26. The method of claim 19, wherein the subject is a human.

* * * * *

UNITED STATES PATENT AND TRADEMARK OFFICE
CERTIFICATE OF CORRECTION

| | | |
|---|---|---|
| PATENT NO. | : 9,150,522 B2 | Page 1 of 1 |
| APPLICATION NO. | : 14/354302 | |
| DATED | : October 6, 2015 | |
| INVENTOR(S) | : Zhengying Pan et al. | |

It is certified that error appears in the above-identified patent and that said Letters Patent is hereby corrected as shown below:

On the title page item (30) should read

Oct. 25, 2011   (CN) .................. 201110327240.9

Signed and Sealed this
Nineteenth Day of April, 2016

Michelle K. Lee
*Director of the United States Patent and Trademark Office*